US012698446B2

(12) United States Patent
Karakaya

(10) Patent No.: US 12,698,446 B2
(45) Date of Patent: Aug. 4, 2026

(54) BIFUNCTIONAL CATALYST AND METHOD OF USE FOR HYDROGENATION OF CARBON DIOXIDE TO HYDROCARBONS

(71) Applicant: UT-Battelle, LLC, Oak Ridge, TN (US)

(72) Inventor: Canan Karakaya, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 537 days.

(21) Appl. No.: 18/143,115

(22) Filed: May 4, 2023

(65) Prior Publication Data

US 2023/0357646 A1     Nov. 9, 2023

Related U.S. Application Data

(60) Provisional application No. 63/338,571, filed on May 5, 2022.

(51) Int. Cl.

| | |
|---|---|
| *C07C 29/149* | (2006.01) |
| *B01J 23/10* | (2006.01) |
| *B01J 23/745* | (2006.01) |
| *B01J 35/45* | (2024.01) |
| *B01J 35/70* | (2024.01) |
| *B01J 37/02* | (2006.01) |
| *B01J 37/08* | (2006.01) |
| *C10G 2/00* | (2006.01) |

(52) U.S. Cl.
CPC ............... *C10G 2/50* (2013.01); *B01J 23/10* (2013.01); *B01J 23/745* (2013.01); *B01J 35/45* (2024.01); *B01J 35/733* (2024.01); *B01J 37/0201* (2013.01); *B01J 37/08* (2013.01); *B01J 37/088* (2013.01); *C07C 29/149* (2013.01); *B01J 2235/00* (2024.01); *B01J 2235/15* (2024.01); *B01J 2235/30* (2024.01)

(58) Field of Classification Search
CPC combination set(s) only.
See application file for complete search history.

(56) References Cited

U.S. PATENT DOCUMENTS

| | | | |
|---|---|---|---|
| 11,519,087 | B2 | 12/2022 | Rondinone et al. |
| 2021/0291150 | A1 | 9/2021 | Karakaya et al. |

OTHER PUBLICATIONS

Wu Y. et al., "System Development of Integrated High Temperature and Low Temperature Fischer-Tropsch Synthesis for High Value Chemicals", *Chemical Engineering Research and Design* 131:80-91 (2018).
Zhang Z. et al., "Insights into the Regulation of FeNa Catalysts Modified by Mn Promoter and Their Tuning Effect on the Hydrogenation of CO2 to Light Olefins", *Journal of Catalysis* 390:12-22 (2020).
Zhang Y. et al., "Operando Spectroscopic Study of Dynamic Structure of Iron Oxide Catalysts During CO2 Hydrogenation", *ChemCatChem* 10:1272-1276 (2018).
Zhang X. et al., "Oxidative Dehydrogenation of Ethane Over Co-BaCO3 Catalysts Using CO2 as Oxidant: Effects of Co Promoter", *Catalysis Letters* 117(3-4):140-145 (Sep. 2007).
Behrens M. et al., "The Active Site of Methanol Synthesis Over Cu/ZnO/Al2O3 Industrial Catalysts", Science 336 (6083):893-897 (May 18, 2012).
Bukur D.B. et al., "Activation Studies With a Precipitated Iron Catalyst for Fischer-Tropsch Synthesis", Journal of Catalysis 155:353-365 (1995).
Cao A. et al., "New Insights on CO and CO2 Hydrogenation for Methanol Synthesis: The Key Role of Adsorbate-Adsorbate Interactions on Cu and the Highly Active MgO—Cu Interface", Journal of Catalysis 400:325-331 (2021).
Chernyak S.A. et al., "Sintered Fe/CNT Framework Catalysts for CO2 Hydrogenation into Hydrocarbons", Carbon 168:475-484 (2020).
Choudhary V.R. et al., "Oxidative Coupling of Methane Over Alkaline Earth Oxides Deposited on Commercial Support Precoated With Rare Earth Oxides", Fuel 78:427-437 (1999).
Cracknell A.P. et al., "Understanding Global Climate Change-Modelling the Climatic System and Human Impacts", Second Edition (2022).
Davis B.H. et al., "Fischer-Tropsch Synthesis, Catalysts, and Catalysis", Advances and Applications (2022).
De Smit E. et al., "The Renaissance of Iron-Based Fischer-Tropsch Synthesis: on the Multifaceted Catalyst Deactivation Behaviour", Chem. Soc. Rev. 37:2758-2781 (2008).
Dorner R.W. et al., "C2—C5+ Olefin Production from CO2 Hydrogenation Using Ceria Modified Fe/Mn/K Catalysts", Catalysis Communications 15:88-92 (2011).
Dry M.E., "The Fischer-Tropsch Process: 1950-2000", Catalysis Today 71:227-241 (2002).
Duan C. et al., "Highly Durable, Coking and Sulfur Tolerant, Fuel-Flexible Protonic Ceramic Fuel Cells", Nature 557:217-222 (May 10, 2018).
Friedel R.A. et al., "Composition of Synthetic Liquid Fuels. I. Product Distribution and Analysis of C5—C8 Paraffin Isomers from Cobalt Catalyst", Communications to the Editor, p. 2307(May 1950).
Gholami Z. et al., "Catalytic Performance of Alumina-Supported Cobalt Carbide Catalysts for Low-Temperature Fischer-Tropsch Synthesis", Catalysts 12:1222 (2022).

(Continued)

*Primary Examiner* — Ana Z Muresan
(74) *Attorney, Agent, or Firm* — Scully, Scott, Murphy & Presser, P.C.

(57) ABSTRACT

A method of hydrogenating carbon dioxide to produce one or more hydrocarbons, the method comprising contacting an input gas stream containing carbon dioxide ($CO_2$) and hydrogen ($H_2$) gases with a bifunctional catalyst comprising a metal oxide in combination with a redox active ceramic support, wherein the redox active ceramic support comprises the formula $BaZr_{1-x-y-z}M^1_yM^2_zY_xO_{3-\delta}$, wherein: $0<x\leq0.2$, $0\leq y\leq0.8$, $0\leq z\leq0.8$, $0<(x+y+z)<1$, and $0\leq\delta\leq0.1$, wherein $\delta$ represents oxygen-ion vacancy; $M^1$ and $M^2$ are selected from lanthanide elements, except that $M^2$ may alternatively be a Group 5 transition metal; and the metal oxide is selected from iron oxides and cobalt oxides.

22 Claims, 17 Drawing Sheets

(56)                    References Cited

OTHER PUBLICATIONS

Han J W et al., "Density Functional Theory Study of H and CO Adsorption on Alkali-Promoted Mo2C Surfaces", The Journal of Physical Chemistry 115:6870-6876 (2011).

Herrera G. et al., "Synthesis, Characterization and Electrochemical Properties of Iron-Zirconia Solid Solution Nanoparticles Prepared Using a Sol-Gel Technique", Phys. Chem. Phys. 15:19312-19321 (2013).

Hong T. et al., "Barium Carbonate Nanoparticles as Synergistic Catalysts for the Oxygen Reduction Reaction on La0.6Sr0.4Co0.2Fe0.8O3-δ Solid-Oxide Fuel Cell Cathodes", ChemElectroChem 3:805-813 (2016).

Hong T. et al., "Barium Carbonate Nanoparticle to Enhance Oxygen Reduction Activity of Strontium Doped Lanthanum Ferrite for Solid Oxide Fuel Cell", Journal of Power Sources 278:741-750 (2015).

Jennings D. et al., "The Effect of Ni and Fe on the Decomposition of Yttrium Doped Barium Zirconate Thin Films", Scripta Materialia 201:113948 (2021).

Jennings D. et al., "The Formation of Oriented Barium Carbonate from the Decomposition of Yttria-Doped Barium Zirconate Films", Scripta Materialia 186:401-405 (2020).

Jennings D.M. et al., "Measurement and Characterization of a High-Temperature, Coke-Resistant Bi-Functional Ni/BZY15 Water-Gas-Shift Catalyst Under Stem-Reforming Conditions", Catalysis Letters 148:3592-3607 (2018).

Jiang J. et al., "Manganese-Promoted Fe3O4 Microsphere for Efficient Conversion of CO2 to Light Olefins", Ind. Eng. Chem. Res. 59:2155-2162 (2020).

Jozwiak W.K. et al., "Reduction Behavior of Iron Oxides in Hydrogen and Carbon Monoxide Atmospheres", Applied Catalysis A: General 326:17-27 (2007).

Kamkeng A.D.N. et al., "Transformation Technologies for CO2 Utilisation: Current Status, Challenges and Future Prospects", Chemical Engineering Journal 409:128138 (2021).

Karakaya C. et al., "CO2 Hydrogenation to Hydrocarbons Over Fe/BZY Catalysts", ChemCatChem 14: e202200802 (2022).

Karakaya C. et al., "Kinetics of the Water-Gas Shift Reaction Over Rh/Al2O3 Catalysts", Applied Catalysis A: General 470:31-44 (2014).

Kiwi J. et al., "Oxidative Coupling of Methane. The Effect of Alkali Chlorides on Molybdate Based Catalyst Leading to High Selectivity in C3-Product Formation", Catalysis Letters 18:15-26 (1993).

Kondratenko E.V. et al., "Status and Perspectives of CO2 Conversion into Fuels and Chemicals by Catalytic, Photocatalytic and Electrocatalytic Processes", Energy & Environmental Science 6:3112-3135 (2013).

Lee W J et al., "Recent Trend in Thermal Catalytic Low Temperature CO2 Methanation: A Critical Review", Catalysis Today 368:2-19 (2021).

Lee S-C et al., "Promotion of Hydrocarbon Selectivity in CO2 Hydrogenation by Ru Component", Journal of Molecular Catalysis: A Chemical 210:131-141 (2004).

Li P. et al., "Effect of Dopants on Zirconia Stabilization—An X-Ray Absorption Study: I, Trivalent Dopants", Journal of the American Ceramic Society 77(1):118-128 (Jan. 1994).

Liu B. et al., "Unravelling the New Roles of Na and Mn Promoter in CO2 Hydrogenation Over Fe3O4-Based Catalysts for Enhanced Selectivity to Light α-Olefins", ChemCatChem 10:4718-4732 (2018).

Liu X. et al., "Resolving CO2 Activation and Hydrogenation Pathways Over Iron Carbides from DFT Investigation", Journal of CO2 Utilization 38:10-15 (May 2020).

Masuku C M et al., "Variation of Residence Time With Chain Length for Products in a Slurry-Phase Fischer-Tropsch Reactor", Journal of Catalysis 287:93-101 (2012).

Modak A. et al., "Catalytic Reduction of CO2 into Fuels and Fine Chemicals", Green Chem. 22:4002-4033 (2020).

Nash C.P. et al., "Mixed Alcohol Dehydration Over Bronsted and Lewis Acidic Catalysts", Applied Catalysis A: General 510:110-124 (2016).

Olah G.A. et al., "Chemical Recycling of Carbon Dioxide to Methanol and Dimethyl Ether: From Greenhouse Gas to Renewable, Environmentally Carbon Neutral Fuels and Synthetic Hydrocarbons", J. Org. Chem. 74(2):487-498 (Jan. 16, 2009).

Pineau A. et al., "Kinetics of Reduction of Iron Oxides by H2 Part I: Low Temperature Reduction of Hematite", Thermochimica Acta 447:89-100 (2006).

Qiu M. et al., "The Mechanisms for CO2 Reduction Over F-Modified Cu(100) Surfaces With Thermodynamics and Kinetics: A DFT Study", RSC Adv. 10:32569-32580 (2020).

Raupp G.B. et al., "Mossbauer Investigation of Supported Fe and FeNi Catalysts II. Carbides Formed by Fischer-Tropsch Synthesis", Journal of Catalysis 58:348-360 (1979).

Roy S. et al., "Thermochemical CO2 Hydrogenation to Single Carbon Products: Scientific and Technological Challenges", ACS Energy Lett. 3:1938-1966 (2018).

Saeidi S. et al., "Effect of Operating Conditions and Effectiveness Factor on Hydrogenation of CO2 to Hydrocarbons", International Journal of Hydrogen Energy 44:28586-28602 (2019).

Sazinas R. et al., "Effect of CO2 Exposure on the Chemical Stability and Mechanical Properties of BaZrO3-Ceramics", Journal of the American Ceramic Society 99(11):3685-3695 (Nov. 2016).

Sordakis K. et al., "Homogeneous Catalysis for Sustainable Hydrogen Storage in Formic Acid and Alcohols", Chem. Rev. 118:372-433 (2018).

Tada S. et al., "Search for Solid Acid Catalysts Aiming at the Development of Bifunctional Tandem Catalyst for the One-Pass Synthesis of Lower Olefins via CO2 Hydrogenation", International Journal of Hydrogen Energy 46:36721-36730 (2021).

Torres Galvis H.M. et al., "Catalysts for Production of Lower Olefins from Synthesis Gas: A Review", ACS Catal. 3:2130-2149 (2013).

Tu C-S et al., "Thermal Stability of Ba(Zr0.8-xCexY0.2)O2.9 Ceramics in Carbon Dioxide", Journal of Applied Physics 105:103504 (2009).

Wang J. et al., "Synthesis of Lower Olefins by Hydrogenation of Carbon Dioxide Over Supported Iron Catalysts", Catalysis Today 215:186-193 (2013).

Wang W. et al., "Recent Advances in Catalytic Hydrogenation of Carbon Dioxide", Chem. Soc. Rev. 40:3703-3727 (2011).

Wei J. et al., "Directly Converting CO2 into a Gasoline Fuel", Nature Communications 8:15174 (2017).

Willauer H.D. et al., "Modeling and Kinetic Analysis of CO2 Hydrogenation Using a Mn and K-Promoted Fe Catalyst in a Fixed-Bed Reactor", Journal of CO2 Utilization 3-4:56-64 (2013).

BIFUNCTIONAL CATALYST AND METHOD OF USE FOR HYDROGENATION OF CARBON DIOXIDE TO HYDROCARBONS

CROSS REFERENCE TO RELATED APPLICATION

The present application claims benefit of U.S. Provisional Application No. 63/338,571, filed on May 5, 2022, all of the contents of which are incorporated herein by reference.

STATEMENT REGARDING FEDERALLY SPONSORED RESEARCH

This invention was made with government support under Prime Contract No. DE-AC05-00OR22725 awarded by the U.S. Department of Energy. The government has certain rights in the invention.

FIELD OF THE INVENTION

This invention generally relates to methods for the conversion of carbon dioxide into useful products. The invention more particularly relates to catalytic methods for converting carbon dioxide to hydrocarbons.

BACKGROUND OF THE INVENTION

A low-cost and straight-forward means for utilizing carbon dioxide ($CO_2$) as a feedstock for producing valuable end products has been long sought, particularly as carbon dioxide is a growing atmospheric waste product contributing to climate change. Such a process would have the potential to significantly reduce reliance on fossil fuels, which is an important step towards a carbon-neutral future.

However, processes for the efficient conversion of carbon dioxide into valuable products, such as hydrocarbons, remain largely elusive, primarily due to limitations of existing catalysts in their catalytic activity, stability, and selectivity. In most of the known processes, carbon monoxide (CO), a low value product, is produced in primary abundance. Moreover, as well known, $CO_2$ is a very stable molecule, which substantially limits its use as a feedstock. The C=O bond energy is 805 kJ $mol^{-1}$ and the $CO_2$ Gibbs free energy of formation ($\Delta G°_{298}$) is −394.4 kJ $mol^{-1}$. The $CO_2$ Gibbs free energy formation is much lower than that of most hydrocarbons or alcohol products that could be formed via hydrogenation. For this reason, using $CO_2$ as a starting material generally requires a high energy input, which is not cost efficient. Thus, a low energy process using a highly active and selective catalyst to convert $CO_2$ to useful products would be a substantial advance but has not yet been realized.

SUMMARY

The present disclosure is foremost directed to a method for hydrogenating carbon dioxide to produce one or more hydrocarbons, particularly saturated or unsaturated hydrocarbons (e.g., paraffinic or olefinic hydrocarbons) containing at least two or three carbon atoms (i.e., $C_{2+}$ or $C_{3+}$ hydrocarbons). The hydrocarbons are typically composed of only carbon and hydrogen, but may or may not include an oxygen atom, which may result in an ether, alcohol, or ketone (e.g., dimethyl ether, methanol, or acetone). The method achieves this by contacting carbon dioxide gas and hydrogen gas with a bifunctional catalyst containing a metal oxide combined with (incorporated into or admixed with) a redox active support. The method advantageously converts carbon dioxide to hydrocarbon product, such as methane, ethane, and/or propane, with high selectivity and low energy input. The bifunctional catalyst used in the method is also advantageously highly active, coke resistant, and stable.

More particularly, the method entails contacting an input gas stream containing carbon dioxide ($CO_2$) and hydrogen ($H_2$) gases with a bifunctional catalyst containing a metal oxide in combination with a redox active ceramic support, wherein the redox active ceramic support has the formula: $BaZr_{1-x-y-z}M^1_yM^2_zY_xO_{3-\delta}$, wherein: $0<x\leq0.2$, $0\leq y\leq0.8$, $0\leq z\leq0.8$, $0<(x+y+z)<1$, and $0\leq\delta\leq0.1$, wherein $\delta$ represents oxygen-ion vacancy; $M^1$ and $M^2$ are independently selected from lanthanide elements, except that $M^2$ may alternatively be or include a Group 5 transition metal; and the metal oxide is selected from iron oxides and cobalt oxides. In some embodiments, $0<x\leq0.2$, $0\leq y\leq0.1$, and $0\leq z\leq0.1$. In separate or further embodiments, the redox active ceramic support has the formula $BaZr_{1-x}Y_xO_{3-\delta}$, wherein $0<x\leq0.2$. In separate or further embodiments, the redox active ceramic support has the formula $BaZr_{0.85}Y_{0.15}O_{3-\delta}$. In separate or further embodiments, $M^1$ and $M^2$ are independently selected from Ce and Yb. In separate or further embodiments, the redox active ceramic support has the formula $BaZr_{1-x-y-z}Ce_yYb_zY_xO_{3-\delta}$, wherein $0<x\leq0.2$, $0\leq y\leq0.8$, $0\leq z\leq0.2$, and $0<(x+y+z)\leq1$. In some embodiments, the contacting occurs at a temperature in a range of 250° C. to 450° C., or a range of 300° C. to 450° C., or a range of 350° C. to 450° C. In some embodiments, the $CO_2$ and $H_2$ gases are present in the contacting step in a $CO_2$:$H_2$ ratio of 0.1 to 1 or 0.3 to 1. In some embodiments, the $CO_2$ and $H_2$ gases are at a pressure of 10-100 atm or 20-50 atm when contacting the bifunctional catalyst. In some embodiments, the $CO_2$ and $H_2$ gases make contact with the bifunctional catalyst for a gas-phase residence time of 1 second to 24 hours, 1 second to 12 hours, 1 second to 6 hours, 1 second to 2 hours, 1 second to 1 hour, 1 second to 30 minutes, 1 second to 10 minutes, 1 second to 5 minutes, 1 second to 1 minute, 1 second to 30 seconds, 1 minute to 24 hours, 1 minute to 12 hours, 1 minute to 2 hours, 1 minute to 1 hour, 1 hour to 40 hours, 1 hour to 30 hours, 10 hours to 40 hours, or 10 hours to 3 hours. In separate or further embodiments, the bifunctional catalyst contains 0.1-90 wt % or 10-50 wt % of the metal oxide. In separate or further embodiments, the bifunctional catalyst is contained in a packed-bed reactor.

BRIEF DESCRIPTION OF THE FIGURES

FIG. 1A is a graph showing equilibrium predictions of the temperature and pressure dependence of $CO_2$ conversion for $CH_3OH$ formation. FIG. 1B is a graph showing selectivity as function of temperature at 100 bar with a stoichiometric feed of $CO_2/H_2=1/3$. The equilibrium calculation includes DME and CO as two competitive carbon-containing species.

FIG. 2A is a graph showing equilibrium predictions of $CO_2$ conversion to form $CH_4$ and CO as functions of temperature at 1 bar. FIG. 2B is a graph showing pressure dependence of carbon selectivity as a function of temperature and pressure. The only carbon species considered in the thermodynamic calculations are CO and $CH_4$.

FIG. 3A is a graph showing equilibrium predictions of $CO_2$ conversion to form $CH_4$, CO, and $C_2$-$C_4$ hydrocarbons as a function of temperature at 30 bar. FIG. 3B is a graph showing $CH_4$ and CO selectivity for varying CO$_2$/H$_2$ ratios as a function of temperature. The line thickness represents the H$_2$ partial pressure.

Figures 4A, 4B:
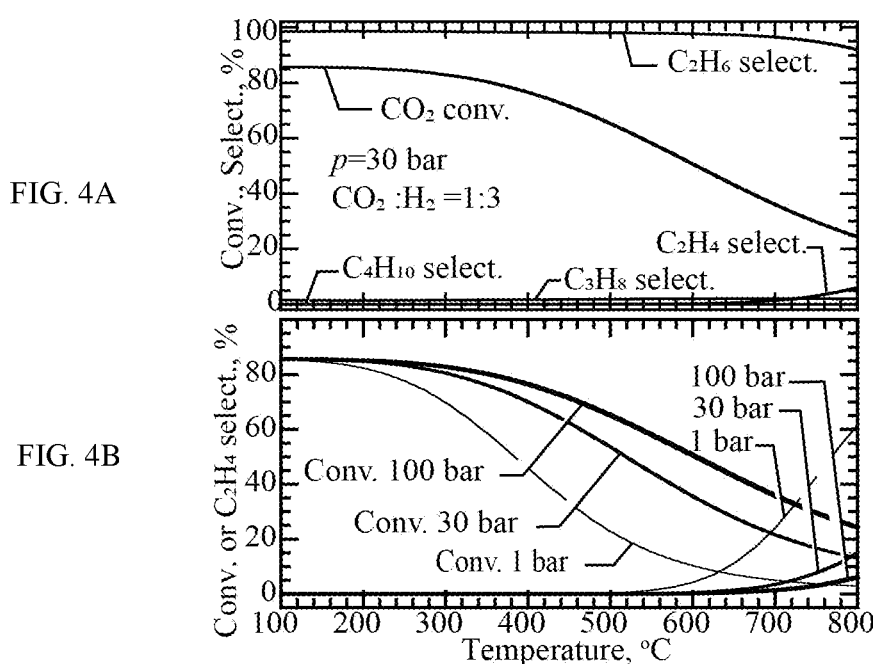

FIGS. 4A-4B. Graphs showing equilibrium predictions of CO$_2$ conversion to form C$_{2+}$ hydrocarbons, wherein CH$_4$ and CO are not included in the calculations. FIG. 4A is a graph showing CO$_2$ conversion, and C$_2$H$_4$, C$_2$H$_6$, C$_3$H$_6$, and C$_4$H$_{10}$ selectivity as a function of temperature at 30 bar. FIG. 4B is a graph showing CO$_2$ conversion and C$_2$H$_4$ selectivity as a function of temperature and pressure.

Figure 5:
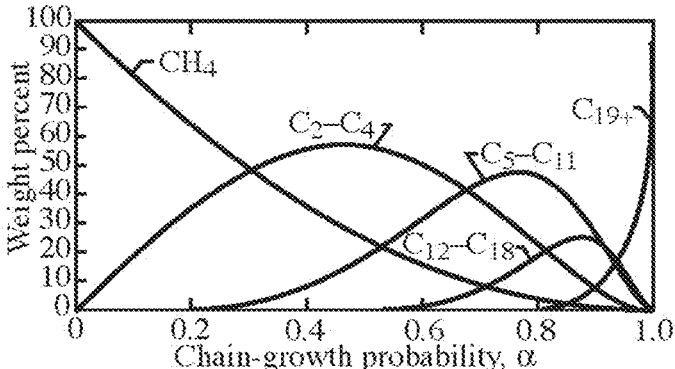

FIG. 5. Anderson-Schultz-Flory diagram showing maximum hydrocarbon selectivities as functions of chain-growth probability.

Figure 6:
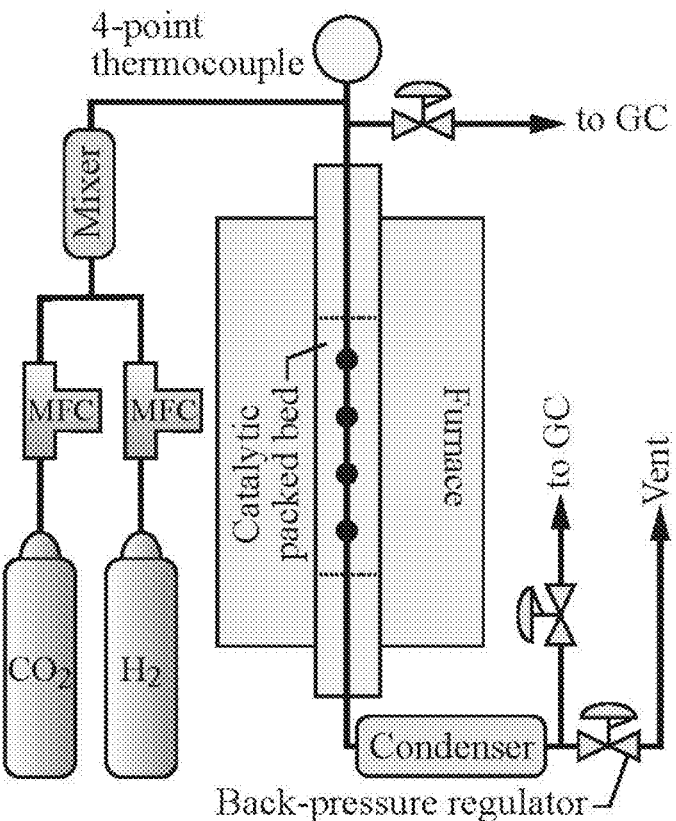

FIG. 6. Process flow diagram for the packed-bed reactor experiments. Feed gases are controlled by mass-flow controllers (MFC) and are premixed before entering the reactor. The reactor pressure is controlled with a back-pressure regulator. The packed bed is oriented vertically.

Figure 7:
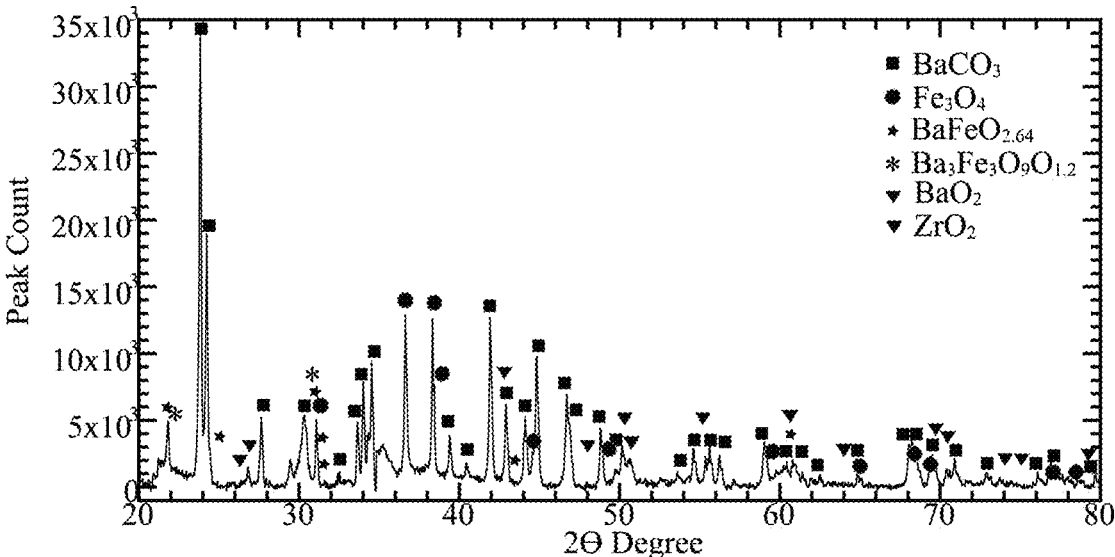

FIG. 7. XRD spectrum of fresh Fe/BZY15 catalyst sample with peaks labeled for the most likely phases identified by commercial software.

Figure 8:
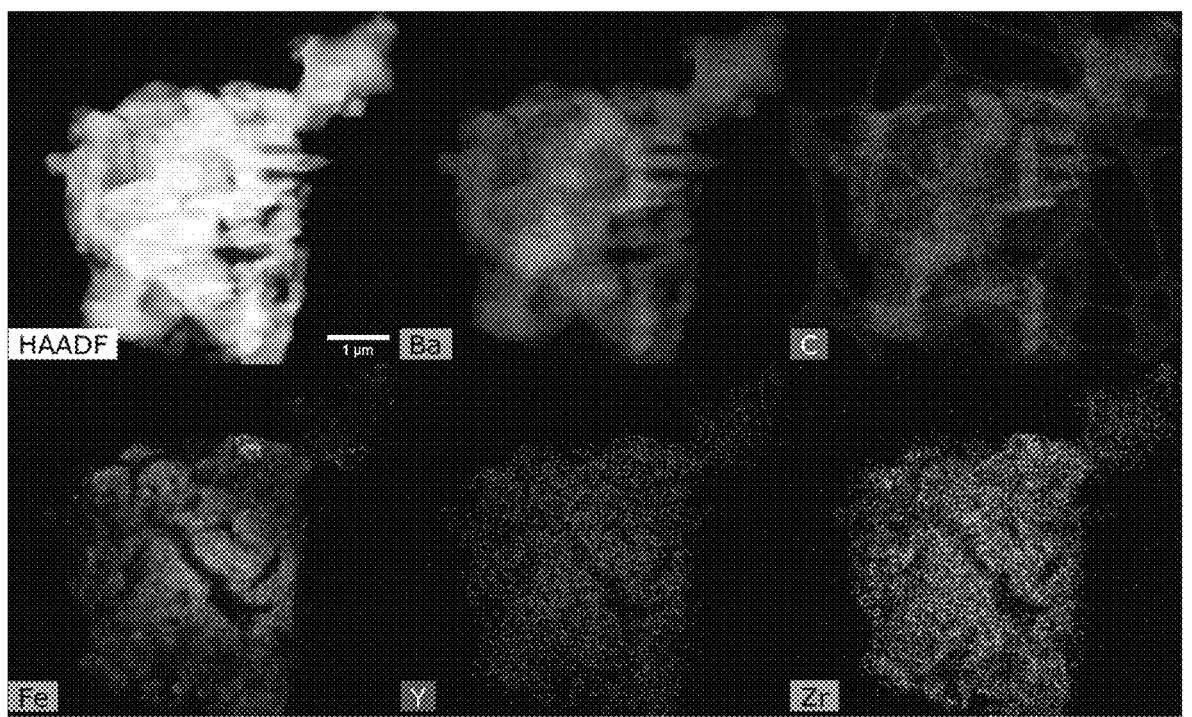

FIG. 8. STEM/EDS map of a particle that shows the distribution of elements in the fresh sample. Barium carbonate and zirconia particles are present, in addition to Fe-rich particles. The upper left image was obtained from High Angular Annular Dark Field (HAADF).

Figure 9:
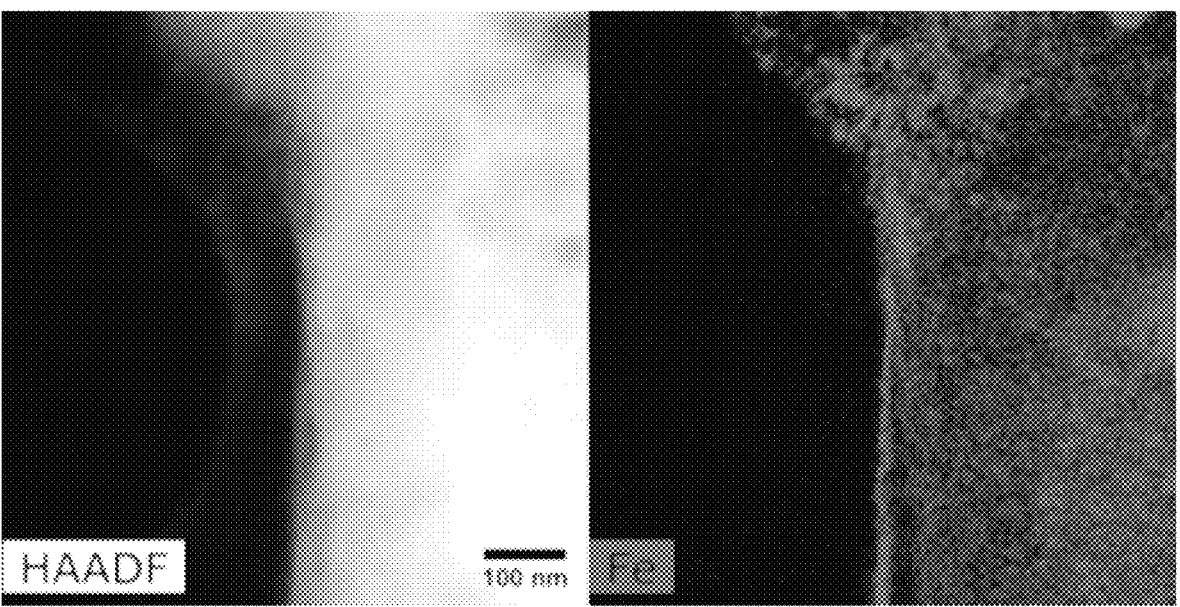

FIG. 9. STEM/HAADF image (left) and corresponding Fe EDS map (right), showing a clear layer of Fe-rich particles on the surface of the fresh catalyst. The XRD results in FIG. 7 indicate that the particles are likely Fe$_3$O$_4$.

Figure 10:
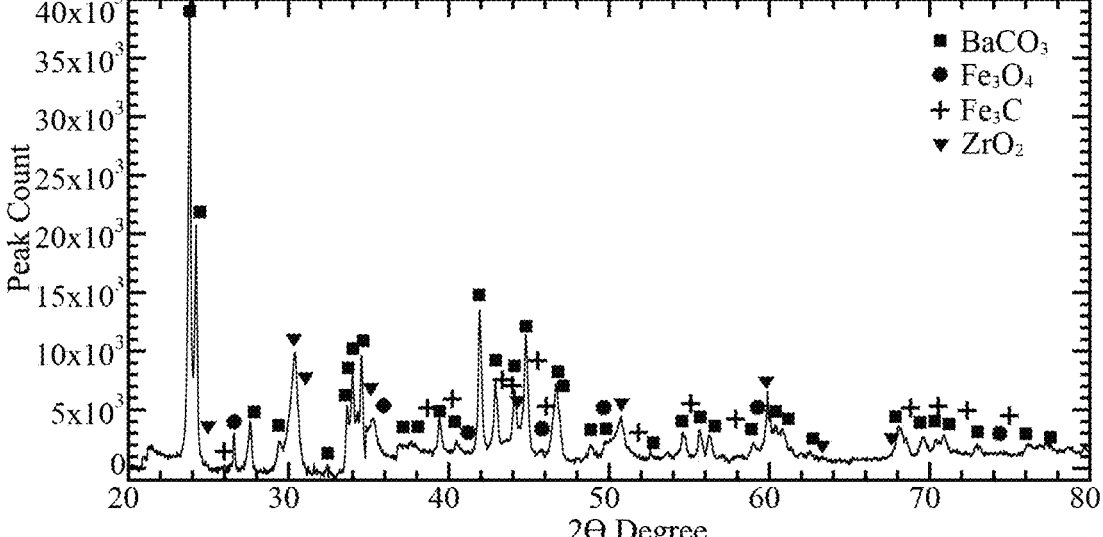

FIG. 10. XRD spectrum of spent Fe/BZY sample with peaks labeled for the most likely phases identified by commercial software.

Figure 11:
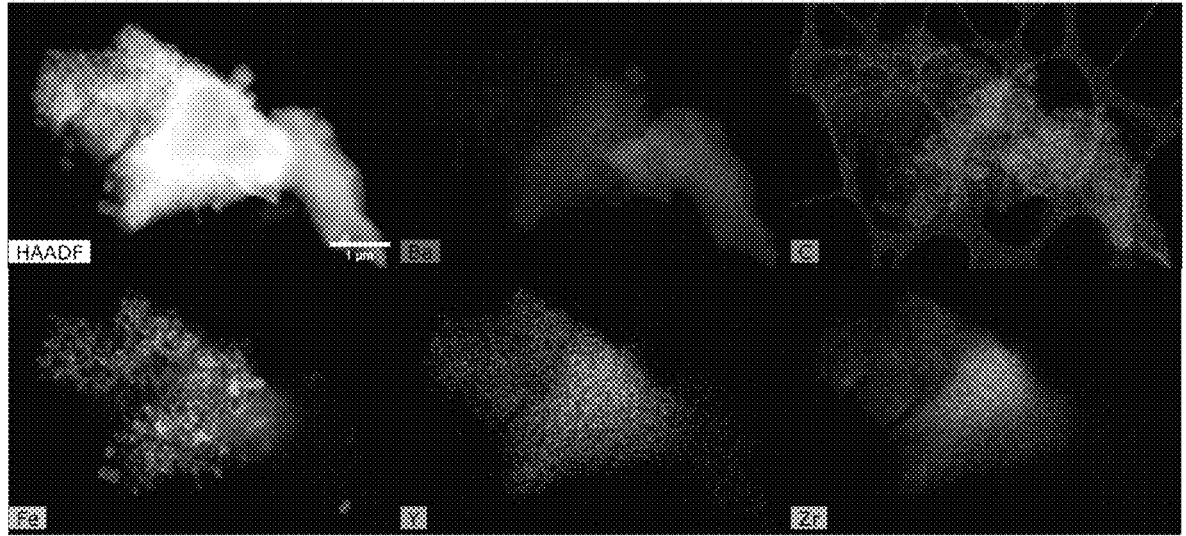

FIG. 11. STEM/EDS map of a particle that shows the distribution of elements in the spent sample. Fe-rich particles are clustered around the zirconia half of the particle.

Figures 12A, 12B:
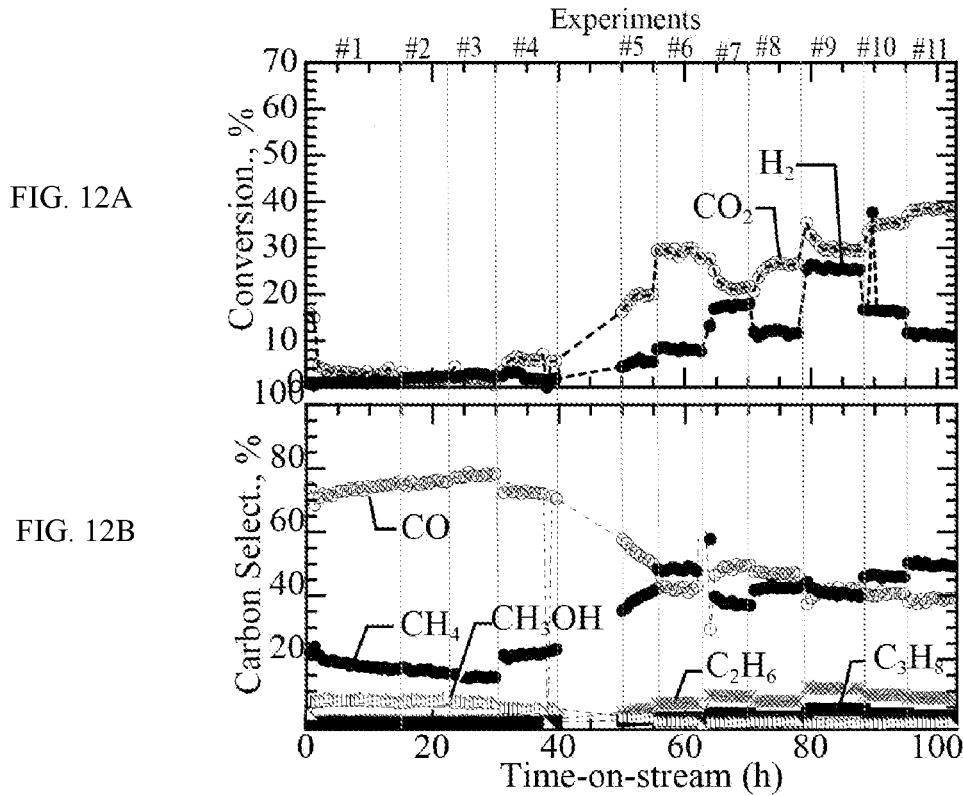

FIGS. 12A-12B. Graphs showing transient activity measurement for CO$_2$ hydrogenation. FIG. 12A shows results for CO$_2$ and H$_2$ conversion. FIG. 12B shows results for carbon selectivity. Table 1 lists experimental conditions for each time interval. Although not shown, small levels of C$_2$H$_4$, C$_3$H$_6$, C$_4$H$_{10}$, and acetone were also detected.

Figure 13:
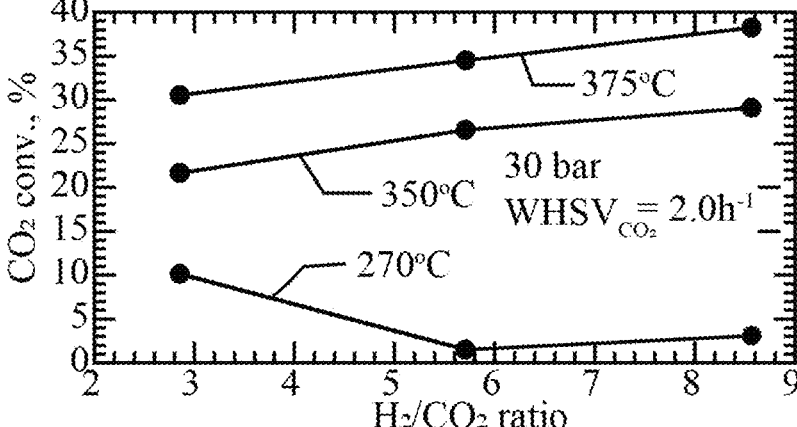

FIG. 13. Graph showing effect of H$_2$/CO$_2$ ratio on CO$_2$ conversion at different temperatures.

Figure 14:
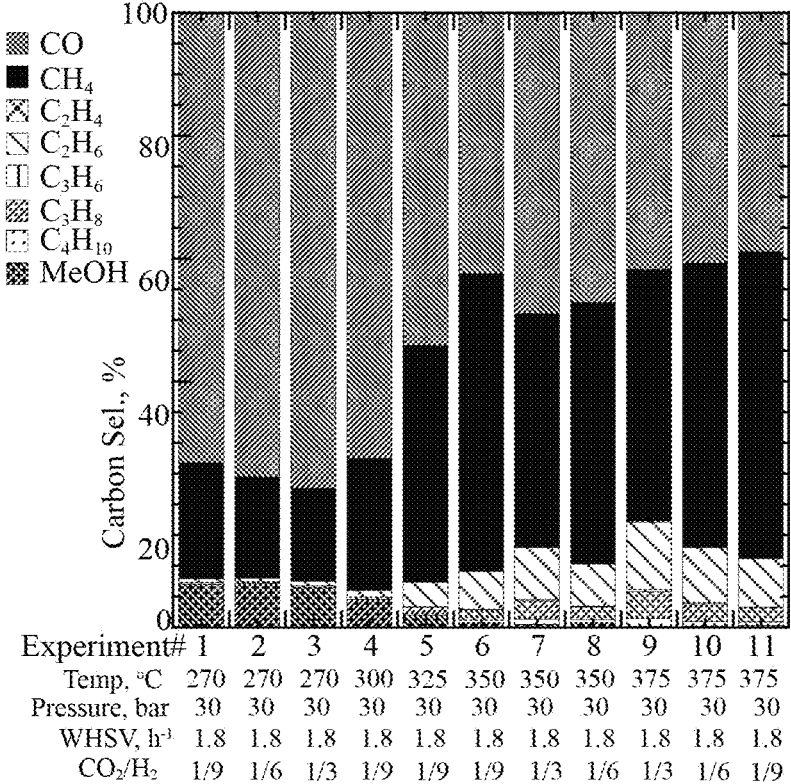

FIG. 14. Bar chart showing the effect of H$_2$/CO$_2$ ratio on CO$_2$ conversion at different temperatures.

Figure 15:
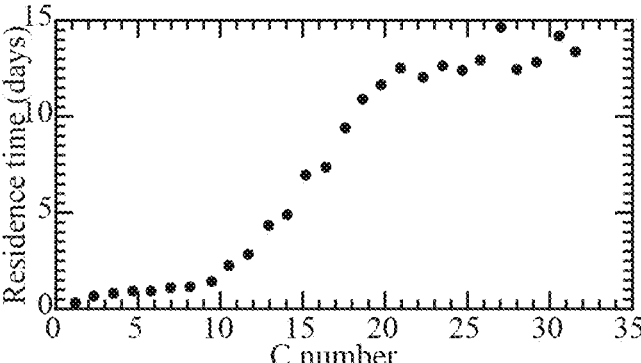

FIG. 15. Graph showing change in carbon number as function of residence time in a Fischer-Tropsch reactor. The reaction was conducted at 220° C. and 20 bar in a slurry FT reactor. The CO$_2$/H$_2$ feed ratio was 1/2.

Figures 16A, 16B, 16C:
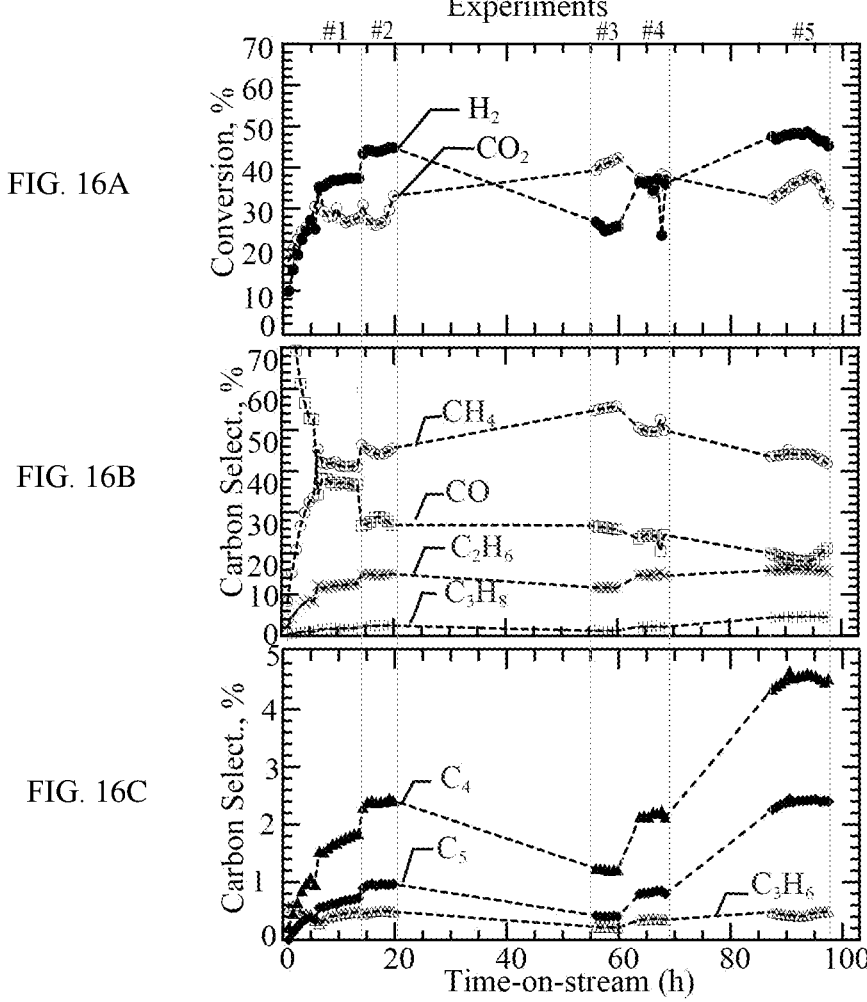

FIGS. 16A-16C. Graphs showing time-on-stream activity measurements for CO$_2$ hydrogenation at varying residence times and CO$_2$/H$_2$ ratios. The reactor conditions were 375° C. and 30 bar. FIG. 16A is a plot of the calculated CO$_2$ and H$_2$ conversions. FIG. 16B is a plot of the carbon selectivities of major carbon species C$_2$-C$_3$. FIG. 16C is a plot of the carbon selectivities of higher hydrocarbon C$_{3+}$ species.

Figure 17:
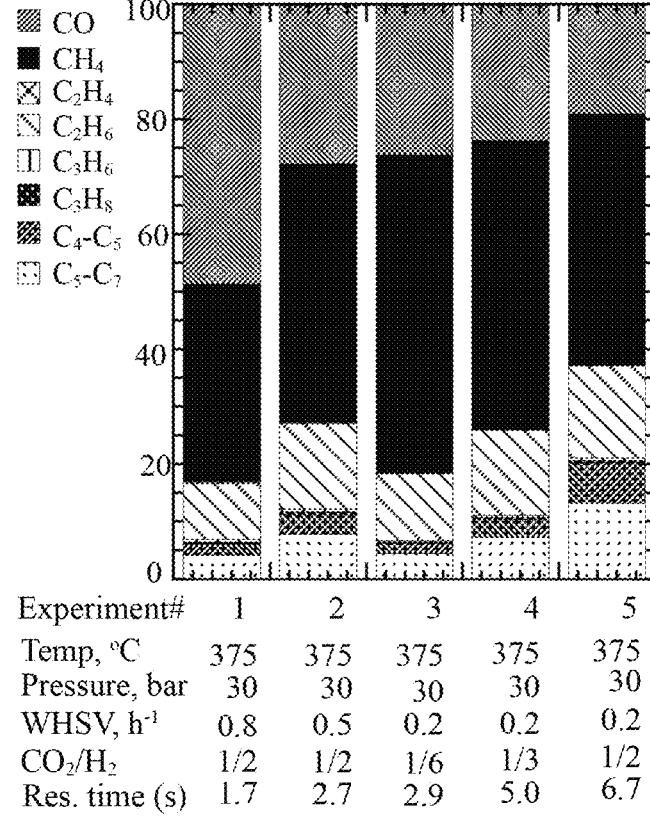

FIG. 17. Bar chart showing the effect of H$_2$/CO$_2$ ratio and residence time on carbon selectivities.

DETAILED DESCRIPTION

In a primary aspect, the present disclosure is directed to a method of hydrogenating carbon dioxide (CO$_2$) to produce one or more hydrocarbons. In the method, an input gas stream containing carbon dioxide and hydrogen (H$_2$) gases is contacted with a bifunctional catalyst containing a metal oxide in combination with a redox active ceramic support.

For purposes of the present disclosure, the redox active ceramic support has the formula BaZr$_{1-x-y-z}$M$^1_y$M$^2_z$Y$_x$O$_{3-\delta}$, wherein: $0 < x \leq 0.2$, $0 \leq y \leq 0.8$, $0 \leq z \leq 0.8$, $0 \leq (x+y+z) < 1$, and $0 \leq \delta \leq 0.1$, wherein $\delta$ represents oxygen-ion vacancy; M$^1$ and M$^2$ are selected from lanthanide elements, except that M$^2$ may alternatively be or include a Group 5 transition metal; and the metal oxide is selected from iron oxides and cobalt oxides. The symbol Zr corresponds to zirconium, and the symbol Y corresponds to yttrium. In some embodiments, the bifunctional catalyst is used by itself, without a secondary support or diluent, when contacting the input gas stream. In other embodiments, the bifunctional catalyst is admixed with, coated onto, or incorporated into a secondary support material or diluent when contacting the input gas stream. The secondary support material or diluent may be any of the support materials or diluents known in the art, such as, for example, a carbon or carbide material, such as silicon carbide (SiC).

The variables M$^1$ and M$^2$ are selected from any of the lanthanide elements. As well known, the lanthanide elements correspond to elements having an atomic number of 57 to 71, i.e., from lanthanum (La) to lutetium (Lu). Thus, M$^1$ and/or M$^2$ may be selected from any of La, Ce, Pr, Nd, Pm, Sm, Eu, Gd, Tb, Dy, Ho, Er, Tm, Yb, and Lu, or subset thereof. In some embodiments, M$^1$ and/or M$^2$ are selected from Ce and Yb. In some embodiments, M$^1$ and M$^2$ are not present (i.e., y and z are both 0). In other embodiments, M$^1$ is present (i.e., y is greater than 0) while M$^2$ is not present (i.e., z is 0). In other embodiments, M$^1$ and M$^2$ are both present (i.e., y and z are both greater than 0), in which case M$^1$ and M$^2$ are different lanthanide elements. In some embodiments, M$^1$ may be selected as a lanthanide and M$^2$ may be selected as a Group 5 transition metal (i.e., V, Nb, or Ta) or M$^2$ may represent a Group 5 transition metal and a lanthanide element in a combined molar amount z.

The variable x corresponds to the molar amount of yttrium (Y). The variable x is typically greater than 0 and less than or equal to 0.2, i.e., $0 < x \leq 0.2$. In different embodiments, x may be, for example, 0.01, 0.02, 0.05, 0.07, 0.1, 0.12, 0.15, 0.17, or 0.2, or x can be in a range bounded by any two of the foregoing values, either inclusively or exclusively. Some examples of possible ranges for x include: $0 < x \leq 0.2$, $0 < x \leq 0.17$, $0 < x \leq 0.15$, $0 < x \leq 0.12$, $0 < x \leq 0.1$, $0 < x \leq 0.07$, $0 < x \leq 0.05$, $0 < x \leq 0.02$, $0.01 \leq x \leq 0.2$, $0.01 \leq x \leq 0.17$, $0.01 \leq x \leq 0.15$, $0.01 \leq x \leq 0.12$, $0.01 \leq x \leq 0.1$, $0.01 \leq x \leq 0.07$, $0.01 \leq x \leq 0.05$, $0.02 \leq x \leq 0.2$, $0.02 \leq x \leq 0.17$, $0.02 \leq x \leq 0.15$, $0.02 \leq x \leq 0.12$, $0.02 \leq x \leq 0.1$, $0.02 \leq x \leq 0.07$, $0.02 \leq x \leq 0.05$, $0.05 \leq x \leq 0.2$, $0.05 \leq x \leq 0.17$, $0.05 \leq x \leq 0.15$, $0.05 \leq x \leq 0.12$, $0.05 \leq x \leq 0.1$, $0.1 \leq x \leq 0.2$, $0.1 \leq x \leq 0.17$, $0.1 \leq x \leq 0.15$, $0.1 \leq x \leq 0.12$, $0.12 \leq x \leq 0.2$, $0.12 \leq x \leq 0.17$, $0.12 \leq x \leq 0.15$, and $0.15 \leq x \leq 0.2$.

The variable y corresponds to the molar amount of M$^1$. The variable y is typically greater than or equal to 0 and less than or equal to 0.8, i.e., $0 \leq y \leq 0.8$. In some embodiments, the variable y is greater than or equal to 0 and less than or equal to 0.1, i.e., $0 \leq y \leq 0.1$. In different embodiments, y may be, for example, 0, 0.01, 0.02, 0.05, 0.07, 0.1, 0.2, 0.3, 0.4, 0.5, 0.6, 0.7, or 0.8, or y may be in a range bounded by any two of the foregoing values, either inclusively or exclusively. Some examples of possible ranges for y include: $0 \leq y \leq 0.8$, $0 \leq y \leq 0.7$, $0 \leq y \leq 0.6$, $0 \leq y \leq 0.5$, $0 \leq y \leq 0.4$, $0 \leq y \leq 0.3$, $0 \leq y \leq 0.2$, $0 \leq y \leq 0.1$, $0 \leq y \leq 0.07$, $0 \leq y \leq 0.05$, $0 \leq y \leq 0.02$, $0 \leq y \leq 0.01$, $0 < y \leq 0.8$, $0 < y \leq 0.7$, $0 < y \leq 0.6$, $0 < y \leq 0.5$, $0 < y \leq 0.4$, $0 < y \leq 0.3$, $0 < y \leq 0.2$, $0 < y \leq 0.1$, $0 < y \leq 0.07$, $0 < y \leq 0.05$, $0 < y \leq 0.02$, $0 < y \leq 0.01$, $0.01 \leq y \leq 0.8$, $0.01 \leq y \leq 0.7$, $0.01 \leq y \leq 0.6$, $0.01 \leq y \leq 0.5$, $0.01 \leq y \leq 0.4$, $0.01 \leq y \leq 0.3$, $0.01 \leq y \leq 0.2$, $0.01 \leq y \leq 0.1$, $0.01 \leq y \leq 0.07$, $0.01 \leq y \leq 0.05$, $0.01 \leq y \leq 0.02$, $0.05 \leq y \leq 0.8$, 0.05≤y≤0.7, 0.05≤y≤0.6, 0.05≤y≤0.5, 0.05≤y≤0.4, 0.05≤y≤0.3, 0.05≤y≤0.2, 0.05≤y≤0.1, 0.05≤y≤0.07, 0.1≤y≤0.8, 0.1≤y≤0.7, 0.1≤0.6, 0.1≤y≤0.5, 0.1≤y≤0.4, 0.1≤y≤0.3, and 0.1≤y≤0.2.

The variable z corresponds to the molar amount of $M^2$. The variable z is typically greater than or equal to 0 and less than or equal to 0.8, i.e., $0 \leq z \leq 0.8$. In some embodiments, the variable z is greater than or equal to 0 and less than or equal to 0.1, i.e., $0 \leq z \leq 0.1$. In different embodiments, z may be, for example, 0, 0.01, 0.02, 0.05, 0.07, 0.1, 0.2, 0.3, 0.4, 0.5, 0.6, 0.7, or 0.8, or z can be in a range bounded by any two of the foregoing values, either inclusively or exclusively. Some examples of possible ranges for z include: 0≤z≤0.8, 0≤z≤0.7, 0≤z≤0.6, 0≤z≤0.5, 0≤z≤0.4, 0≤z≤0.3, 0≤z≤0.2, 0≤z≤0.1, 0≤z≤0.07, 0≤z≤0.05, 0≤z≤0.02, 0≤z≤0.01, 0<z≤0.8, 0<z≤0.7, 0<z≤0.6, 0<z≤0.5, 0<z≤0.4, 0<z≤0.3, 0<z≤0.2, 0<z≤0.1, 0<z≤0.07, 0<z≤0.05, 0<z≤0.02, 0<z≤0.01, 0.01≤z≤0.8, 0.01≤z≤0.7, 0.01≤z≤0.6, 0.01≤z≤0.5, 0.01≤z≤0.4, 0.01≤z≤0.3, 0.01≤z≤0.2, 0.01≤z≤0.1, 0.01≤z≤0.07, 0.01≤z≤0.05, 0.01≤z≤0.02, 0.05≤z≤0.8, 0.05≤z≤0.7, 0.05≤z≤0.6, 0.05≤z≤0.5, 0.05≤z≤0.4, 0.05≤z≤0.3, 0.05≤z≤0.2, 0.05≤z≤0.1, 0.05≤z≤0.07, 0.1≤z≤0.8, 0.1≤z≤0.7, 0.1≤z≤0.6, 0.1≤z≤0.5, 0.1≤z≤0.4, 0.1≤z≤0.3, and 0.1≤z≤0.2.

The total molar amount of x, y, and z is greater than 0 and less than 1, i.e., $0 < (x+y+z) < 1$. In different embodiments, x+y+z may be, for example, 0.1, 0.15, 0.2, 0.25, 0.3, 0.35, 0.4, 0.45, 0.5, 0.55, 0.6, 0.65, 0.7, 0.75, 0.8, 0.85, 0.9, or 0.95, or x+y+z can be in a range bounded by any two of the foregoing values, either inclusively or exclusively. Some examples of possible ranges for x+y+z include: 0<(x+y+z)<1, 0<(x+y+z)≤0.8, 0<(x+y+z)≤0.5, 0<(x+y+z)≤0.3, 0<(x+y+z)≤0.2, 0<(x+y+z)≤0.15, 0<(x+y+z)≤0.1, 0.1≤(x+y+z)<1, 0.1≤(x+y+z)≤0.8, 0.1≤(x+y+z)≤0.5, 0.1≤(x+y+z)≤0.3, 0.1≤(x+y+z)≤0.2, 0.1≤(x+y+z)≤0.15, 0.2≤(x+y+z)<1, 0.2≤(x+y+z)≤0.8, 0.2≤(x+y+z)≤0.5, and 0.2≤(x+y+z)≤0.3.

The variable δ represents the oxygen-ion vacancy and is typically greater than or equal to 0 and less than or equal to 0.1, i.e., and $0 < \delta \leq 0.1$. Often, δ is precisely or about 0.05.

In some embodiments, $M^1$ and $M^2$ are not present, which results in the redox active ceramic support having the following formula: $BaZr_{1-x}Y_xO_{3-\delta}$, wherein $0 < x \leq 0.2$, as described above. Some particular examples of redox active ceramic support compositions within the foregoing formula include $BaZr_{0.95}Y_{0.05}O_{3-\delta}$, $BaZr_{0.9}Y_{0.1}O_{3-\delta}$, $BaZr_{0.85}Y_{0.15}O_{3-\delta}$, and $BaZr_{0.8}Y_{0.2}O_{3-\delta}$.

In some embodiments, $M^1$ is present without $M^2$, which results in the redox active ceramic support having the following formula: $BaZr_{1-x-y}M^1_yY_xO_{3-\delta}$, wherein $0 < x \leq 0.2$ and $0 < y \leq 0.8$ and $M^1$ is a lanthanide element, particularly Ce and Yb, all as described above. Some sub-formulas of redox active ceramic support compositions within the foregoing formula include $BaZr_{1-x-y}Ce_yY_xO_{3-\delta}$, $BaZr_{1-x-y}Pr_yY_xO_{3-\delta}$, $BaZr_{1-x-y}Yb_yY_xO_{3-\delta}$, $BaZr_{1-x-y}Nd_yY_xO_{3-\delta}$, $BaZr_{1-x-y}Sm_yY_xO_{3-\delta}$, $BaZr_{1-x-y}Dy_yY_xO_{3-\delta}$, and $BaZr_{1-x-y}Lu_yY_xO_{3-\delta}$.

In some embodiments, $M^1$ and $M^2$ are both present, which results in the redox active ceramic support having the following formula: $BaZr_{1-x-y-z}M^1_yM^2_zY_xO_{3-\delta}$, wherein $0 < x \leq 0.2$, $0 < y \leq 0.8$, $0 < z \leq 0.8$, $0 < (x+y+z) < 1$, as described above. In some embodiments, $M^1$ and $M^2$ are selected from lanthanide elements, particularly Ce and Yb, as described above. Some sub-formulas of redox active ceramic support compositions within the foregoing formula include $BaZr_{1-x-y-z}Ce_yYb_zY_xO_{3-\delta}$, $BaZr_{1-x-y-z}Ce_yNd_zY_xO_{3-\delta}$, $BaZr_{1-x-y-z}Ce_ySm_zY_xO_{3-\delta}$, $BaZr_{1-x-y-z}Ce_yDy_zY_xO_{3-\delta}$, $BaZr_{1-x-y-z}Ce_yHo_zY_xO_{3-\delta}$, $BaZr_{1-x-y-z}Ce_yEr_zY_xO_{3-\delta}$, $BaZr_{1-x-y-z}Ce_yLu_zY_xO_{3-\delta}$, $BaZr_{1-x-y-z}Yb_yNd_zY_xO_{3-\delta}$, $BaZr_{1-x-y-z}Yb_ySm_zY_xO_{3-\delta}$, $BaZr_{1-x-y-z}Yb_yDy_zY_xO_{3-\delta}$, $BaZr_{1-x-y-z}Yb_yHo_zY_xO_{3-\delta}$, $BaZr_{1-x-y-z}Yb_yEr_zY_xO_{3-\delta}$, and $BaZr_{1-x-y-z}Yb_yLu_zY_xO_{3-\delta}$. A specific example of such a composition is $BaCe_{0.7}Zr_{0.1}Y_{0.1}Yb_{0.1}O_{2.95}$. As noted earlier above, in other embodiments, $M^1$ is a lanthanide element and $M^2$ is selected as a Group 5 transition metal (i.e., V, Nb, or Ta). Some sub-formulas of redox active ceramic support compositions within the foregoing formula include $BaZr_{1-x-y-z}Ce_yNb_zY_xO_{3-\delta}$, $BaZr_{1-x-y-z}Yb_yNb_zY_xO_{3-\delta}$, $BaZr_{1-x-y-z}Nd_yNb_zY_xO_{3-\delta}$, $BaZr_{1-x-y-z}Sm_yNb_zY_xO_{3-\delta}$, $BaZr_{1-x-y-z}Dy_yNb_zY_xO_{3-\delta}$, $BaZr_{1-x-y-z}Lu_yNb_zY_xO_{3-\delta}$, $BaZr_{1-x-y-z}Ce_yV_zY_xO_{3-\delta}$, and $BaZr_{1-x-y-z}Ce_yTa_zY_xO_{3-\delta}$.

In yet other embodiments, $M^1$ is a lanthanide element and $M^2$ represents a Group 5 transition metal (i.e., V, Nb, or Ta) in combination with a lanthanide element, which results in the redox active ceramic support having the following formula: $BaZr_{1-x-y-z}M^1_yM^{2a}_{z1}M^{2b}_{z2}Y_xO_{3-\delta}$, wherein $M^{2a}$ is a lanthanide element, $M^{2b}$ is a Group 5 transition metal, $0 < x \leq 0.2$, $0 < y \leq 0.8$, $0 < (z1+z2) \leq 0.8$, and $0 < (x+y+z1+z2) < 1$. Some sub-formulas of such redox active ceramic support compositions within the foregoing formula include $BaZr_{1-x-y-z}Ce_yPr_{za}Nb_{zb}Y_xO_{3-\delta}$, $BaZr_{1-x-y-z}Ce_yYb_{za}Nb_{zb}Y_xO_{3-\delta}$, $BaZr_{1-x-y-z}Ce_yNd_{za}Nb_{zb}Y_xP_{3-\delta}$, $BaZr_{1-x-y-z}Ce_ySm_{za}Nb_{zb}Y_xO_{3-\delta}$, $BaZr_{1-x-y-z}Ce_yTb_{za}Nb_{zb}Y_xO_{3-\delta}$, $BaZr_{1-x-y-z}Yb_yPr_{za}Nb_{zb}Y_xO_{3-\delta}$, $BaZr_{1-x-y-z}Yb_yNd_{za}Nb_{zb}Y_xO_{3-\delta}$, $BaZr_{1-x-y-z}Yb_ySm_{za}Nb_{zb}Y_xO_{3-\delta}$, and $BaZr_{1-x-y-z}Yb_yTb_{za}Nb_{zb}Y_xO_{3-\delta}$.

As noted earlier above, the bifunctional catalyst also includes a metal oxide. In the bifunctional catalyst, the metal oxide is in combination with the redox active ceramic support, wherein the metal oxide is selected from iron oxides and cobalt oxides. The term "in combination with" includes being in admixture with or incorporated into (i.e., impregnated into) the redox active ceramic support. The bifunctional catalyst typically includes at least 0.1 wt % and up to or less than 90 wt % of the metal oxide. In different embodiments, the bifunctional catalyst includes precisely, about, or at least, for example, 0.1, 0.5, 1, 2, 5, 10, 20, 30, 40, 50, 60, 70, 80, or 90 wt % of the metal oxide, or an amount of the metal oxide within a range bounded by any two of the foregoing values (e.g., 0.1-90 wt %, 0.5-90 wt %, 1-90 wt %, 5-90 wt %, 10-90 wt %, 20-90 wt %, 30-90 wt %, 40-90 wt %, 50-90 wt %, 60-90 wt %, 0.1-70 wt %, 0.5-70 wt %, 1-70 wt %, 5-70 wt %, 10-70 wt %, 20-70 wt %, 30-70 wt %, 40-70 wt %, 50-70 wt %, 60-70 wt %, 0.1-50 wt %, 0.5-50 wt %, 1-50 wt %, 5-50 wt %, 10-50 wt %, 20-50 wt %, 30-50 wt %, 40-50 wt %, 0.1-30 wt %, 0.5-30 wt %, 1-30 wt %, 5-30 wt %, 10-30 wt %, 20-30 wt %, 0.1-20 wt %, 0.5-20 wt %, 1-20 wt %, 5-20 wt %, 10-20 wt %, 0.1-10 wt %, 0.5-10 wt %, 1-10 wt %, 5-10 wt %, 0.1-5 wt %, 0.5-5 wt %, or 1-5 wt %).

In one set of embodiments, the metal oxide is an iron oxide. The iron in the iron oxide may be in the +2 or +3 state. The iron oxide may have any of the known formulas, e.g., $Fe_2O_3$, $Fe_3O_4$, or FeO, and may be in any of the known phases (e.g., alpha, beta, gamma, or epsilon). The iron oxide may also be an iron oxide-hydroxide. In another set of embodiments, the metal oxide is a cobalt oxide. The cobalt in the cobalt oxide may be in the +2 or +3 state. The cobalt oxide may have any of the known formulas, e.g., $Co_3O_4$, CoO, or $Co_2O_3$, and may be in any of the known phases (e.g., alpha, beta, gamma, or epsilon). The cobalt oxide may also be a cobalt oxide-hydroxide. In some embodiments, the metal oxide is a mixture of an iron oxide and a cobalt oxide. The iron oxide, cobalt oxide, or mixture thereof may or may not be in admixture with another metal oxide, such as a chromium oxide, manganese oxide, nickel oxide, or zinc oxide.

The redox active ceramic support is typically in the form of nanoparticles. The term "nanoparticles," as used herein, generally refers to particles having a size of at least 1, 2, 3, 5, 10, 20, 30, 40, or 50 nm and up to 100, 200, 300, 400, or 500 nm in at least one or two dimensions (or typically all dimensions) of the nanoparticles or a size within a range bounded by any two of the foregoing values (e.g., 1-500 nm, 1-100 nm, 1-50 nm, 10-500 nm, 10-100 nm, or 10-50 nm). In some embodiments, any of the foregoing particle sizes represents an average particle size. In embodiments where the metal oxide is incorporated into the redox active ceramic support, the foregoing sizes correspond to the size of particles of the redox active ceramic support. In embodiments where the metal oxide particles are in admixture with the redox active ceramic support particles, the metal oxide particles and redox active ceramic support particles independently have a size selected from any of the nanoparticle sizes provided above.

The redox active ceramic support described above can be produced by methods well known in the art. In typical embodiments, the support material is prepared by mixing nitrate and/or oxide precursors of metals, and calcining the mixture. The preparation method may entail, for example, mixing barium nitrate, zirconium nitrate, and yttrium oxide in proper molar amounts, typically along with complexing agents (e.g., EDTA) and/or citric acid, to form a gel, which is then dried and calcined at a temperature of 700-1000° C. for 5-12 hours. To incorporate the metal oxide, the as-produced support may then be impregnated with a solution containing an iron and/or cobalt salt (e.g., iron and/or cobalt nitrate), followed by drying and calcination. Alternatively, the as-produced support may be mixed with the metal oxide by mixing methods well known in the art, e.g., ball mixing.

Although the bifunctional catalyst may be used directly after the synthesis described above, in some embodiments, the bifunctional catalyst is subjected to a pretreatment process in which the bifunctional catalyst is contacted with a reducing gas (typically, hydrogen gas or hydrogen-inert gas mixture) at an elevated temperature of 450-600° C. or 450-550° C. or about 500° C. In some embodiments, the pretreatment process further includes a carburization process at an elevated temperature of 450-600° C. in the presence of CO or a hydrocarbon (e.g., $CH_4$, $C_2H_6$, $C_3H_8$, and/or $C_4H_{10}$) and hydrogen gas. The carburization process forms one or more carbides of the metal(s) in the metal oxide, e.g., $Fe_3C$, $Fe_5C_2$, $Co_2C$, and $Co_3C$, or a mixture of any two or more of these.

In the method for hydrogenating carbon dioxide to produce one or more hydrocarbons, an input gas stream containing $CO_2$ and $H_2$ is contacted with the bifunctional catalyst described above. As noted above, the bifunctional catalyst may be used directly after synthesis or after a pretreatment process. When contacting the input gas stream, the bifunctional catalyst may be housed in any suitable reactor design, such as a packed-bed reactor or a fluidized bed reactor.

The $CO_2$ and $H_2$ gases are typically present in the input gas stream in a $CO_2$:$H_2$ molar (or volume) ratio of 0.1 to 1 (i.e., 0.1:1 to 1:1, or equivalently, 1:10 to 1:1). In different embodiments, the input gas stream includes $CO_2$ and $H_2$ gases in a $CO_2$:$H_2$ molar (or volume) ratio of 1:10, 1:9, 1:8, 1:7, 1:6, 1:5, 1:4, 1:3, 1:2, or 1:1, or a ratio within a range bounded by any two of the foregoing ratios (e.g., 1:10-1:1, 1:5-1:1, 1:4-1:1, or 1:3-1:1).

The input gas stream containing the $CO_2$ and $H_2$ gases may be at ambient pressure (about 1 atm) or at an elevated pressure above 1 atm when contacting the bifunctional catalyst. When an elevated pressure is used, the pressure may be precisely or at least, for example, 2, 5, 10, 20, 30, 40, 50, 60, 70, 80, 90, 100, 110, 120, 130, 140, 150, 160, 170, 180, 190, or 200 atm, or a pressure within a range bounded by any two of the foregoing values (e.g., 1-200 atm, 1-150 atm, 1-100 atm, 1-50 atm, 5-200 atm, 5-150 atm, 5-100 atm, 5-50 atm, 10-200 atm, 10-150 atm, 10-100 atm, or 10-50 atm).

When the input gas stream contacts the bifunctional catalyst, the bifunctional catalyst can be at room temperature (typically 18-30° C. or about 25° C.) or an elevated temperature. The input gas stream may or may not also be heated before contacting the catalyst. When an elevated temperature is used, the temperature may be precisely or at least, for example, 40° C., 50° C., 60° C., 70° C., 80° C., 90° C., 100° C., 110° C., 120° C., 150° C., 180° C., 200° C., 250° C., 270° C., 300° C., 350° C., 375° C., 400° C., 450° C., 500° C., 550° C., or 600° C., or a temperature within a range bounded by any two of the foregoing values (e.g., 50-600° C., 100-600° C., 200-600° C., 250-600° C., 270-600° C., 300-600° C., 350-600° C., 375-600° C., 400-600° C., 450-600° C., 50-500° C., 100-500° C., 200-500° C., 250-500° C., 270-500° C., 300-500° C., 350-500° C., 375-500° C., 400-500° C., 450-500° C., 50-450° C., 100-450° C., 200-450° C., 250-450° C., 300-450° C., 350-450° C., 400-450° C., 50-400° C., 100-400° C., 200-400° C., 250-400° C., 270-400° C., 300-400° C., 350-400° C., 50-375° C., 100-375° C., 200-375° C., 250-375° C., 270-375° C., 300-375° C., or 350-375° C.).

The input gas stream makes contact with the bifunctional catalyst for any suitable gas-phase residence time at any of the gas ratios, pressures, or temperatures provided above. The residence time is typically within a range of 1 second to 24 hours, depending on the conditions employed. In some embodiments, the residence time may be longer, e.g., 30, 35, or 40 hours. In different embodiments, and depending on the conditions used, the residence time may be 1 second, 5 seconds, 10 seconds, 30 seconds, 1 minute, 5 minutes, 10 minutes, 30 minutes, 1 hour, 2 hours, 3 hours, 4 hours, 5 hours, 6 hours, 12 hours, 18 hours, or 24 hours, or a residence time within a range bounded by any two of the foregoing values (e.g., 1 second to 24 hours, 1 second to 12 hours, 1 second to 6 hours, 1 second to 2 hours, 1 second to 1 hour, 1 second to 30 minutes, 1 second to 10 minutes, 1 second to 1 minute, 1-30 seconds, 1 minute to 24 hours, 1 minute to 12 hours, 1 minute to 6 hours, 1-40 hours, 1-30 hours, 6-40 hours, 6-30 hours, 6-24 hours, 10-40 hours, 10-30 hours, or 10-24 hours).

The method employs any suitable weight hourly space velocity (WHSV) of $CO_2$, wherein it is known that the WHSV is at least in part determined by the feed content and gas-phase residence time. The WHSV is typically in a range of 0.2-3 $h^{-1}$. In different embodiments, and dependent on the feed content, residence time, and other factors, the WHSV may be precisely or about, for example, 0.2 $h^{-1}$, 0.3 $h^{-1}$, 0.4 $h^{-1}$, 0.5 $h^{-1}$, 0.6 $h^{-1}$, 0.7 $h^{-1}$, 0.8 $h^{-1}$, 0.9 $h^{-1}$, 1 $h^{-1}$, 1.2 $h^{-1}$, 1.4 $h^{-1}$, 1.6 $h^{-1}$, 1.8 $h^{-1}$, 2 $h^{-1}$, 2.2 $h^{-1}$, 2.4 $h^{-1}$, 2.6 $h^{-1}$, 2.8 $h^{-1}$, or 3 $h^{-1}$, or a WHSV within a range bound by any two of the foregoing values (e.g., 0.2-3 $h^{-1}$, 0.2-2.5 $h^{-1}$, 0.2-2 $h^{-1}$, 0.3-3 $h^{-1}$, 0.3-2.5 $h^{-1}$, 0.3-2 $h^{-1}$, 0.4-3 $h^{-1}$, 0.4-2.5 $h^{-1}$, 0.4-2 $h^{-1}$, 0.5-3 $h^{-1}$, 0.5-2.5 $h^{-1}$, 0.5-2 $h^{-1}$, 1-3 $h^{-1}$, 1-2.5 $h^{-1}$, or 1-2 $h^{-1}$).

The method described above results in the production of one or more types of hydrocarbons. Typically, an amount of carbon monoxide (CO) (e.g., 10, 20, 30, 40, 50, or 60 wt % of total product, or within a range therein) is produced along with the hydrocarbon(s). The one or more produced hydrocarbons are typically selected from paraffins, olefins, or combination thereof. Typically, of the hydrocarbons produced, methane is produced in greatest abundance, e.g., at least 15, 20, 25, 30, 35, 40, 45, 50, 55, 60, 65, or 70 wt % of total product, or an amount within a range bounded by any two of the foregoing values. The process typically also produces one or more hydrocarbons containing at least two carbon atoms, i.e., $C_{2+}$ hydrocarbons. Some hydrocarbons containing two carbon atoms include ethane ($C_2H_6$) and ethene ($C_2H_4$). The $C_{2+}$ hydrocarbons typically also include some amount of hydrocarbons containing at least three carbon atoms (i.e., $C_{3+}$ hydrocarbons, such as $C_3H_8$), and may also include some amount of hydrocarbons containing at least four carbon atoms (i.e., $C_{4+}$ hydrocarbons, such as $C_4H_{10}$). The $C_2$ hydrocarbon(s) are typically produced in an amount of precisely, about, or at least, for example, 1, 2, 3, 4, 5, 6, 7, 8, 10, 12, 15, 18, or 20 wt % of total product, or an amount within a range bounded by any two of the foregoing values. The $C_{3+}$ or $C_{4+}$ hydrocarbon(s) are typically produced in an amount of precisely, about, or at least, for example, 1, 2, 3, 4, 5, 6, 7, 8, 9, or 10 wt % of total product, or an amount within a range bounded by any two of the foregoing values.

The carbon dioxide being converted may be produced by any known source of carbon dioxide. The source of carbon dioxide may be, for example, a combustion source (e.g., from burning of fossil fuels in an engine or generator), commercial biomass fermenter, or commercial carbon dioxide-methane separation process for gas wells.

Examples have been set forth below for the purpose of illustration and to describe certain specific embodiments of the invention. However, the scope of this invention is not to be in any way limited by the examples set forth herein.

Examples

Overview

Herein is described a $CO_2$ hydrogenation process in a catalytic laboratory-scale packed-bed reactor using an Fe/BZY15 ($BaZr_{0.85}Y_{0.15}O_{3-\delta}$) catalyst to form hydrocarbons (e.g., $CH_4$, $C_{2+}$) at elevated pressure of 30 bar and temperatures in the range $270 \leq T \leq 375°$ C. The effects of temperature, feed composition (i.e., $CO_2/H_2$ ratio), and residence time (i.e., Weight Hourly Space Velocity (WHSV) were studied to understand the relationship between $CO_2$ conversion and carbon selectivity. Catalyst characterization elucidated the relationships between the catalyst structure, surface adsorbates, and reaction pathways. Thermodynamic analyses guided the experimental conditions and assisted in interpreting results. While the feed composition and temperature influence the product distribution, the results suggest that the higher-carbon ($C_{2+}$) selectivity and yield depend strongly on residence time. The results suggest that the $CO_2$ hydrogenation reaction pathway is similar to Fischer-Tropsch (FT) synthesis. The reaction begins with $CO_2$ activation to form CO, followed by chain-growth reactions similar to the FT process. The $CO_2$ activation depends on the redox activity of the catalyst. However, the carbon chain growth depends primarily on the residence time. As is the case for FT synthesis, high residence time (on the orders of hours) was found to favor a high $C_{2+}$ yield.

The present experiments were directed to developing a catalyst and process to form $C_{2+}$ hydrocarbons via direct $CO_2$ hydrogenation. The methodology addresses the need for understanding the close interactions between kinetic and thermodynamic limitations to design a highly selective and stable catalyst. The Fe/BZY15 catalyst provided a stable $CO_2$ hydrogenation to form $C_2$-$C_4$ olefins and paraffins. Light olefins (i.e., $C_2H_4$ or $C_3H_8$) are the preferred product because of their high market value and versatility as a chemical or fuel.

It is well known that the catalyst metal, metal-support interactions, and microstructure play critical roles in product distribution. Several laboratory-scale studies show significant improvement in producing olefin- and paraffin-range hydrocarbons, but the catalyst stability remains an issue. The present work used 20% $Fe_2O_3$ loaded onto a redox-active BZY15 support that promotes bi-functionality. The active Fe metal provides high redox activity while the BZY15 support provides catalytic stability in hydrocarbon- and CO-containing environments. Using $Fe_2O_3$/BZY15 as the catalyst, the present work provides a catalytic system that permits stable $CO_2$ hydrogenation to form hydrocarbons.

The Fe/BZY15 catalyst showed remarkable catalytic stability while providing high $CO_2$ conversion and $C_{2+}$ hydrocarbon selectivity. The stable coke-free operation was sustained for 100 hours time-on-stream. The present work investigated the effects of operating conditions on product distributions. The analysis considered theoretical limits, highlighting technical challenges. Packed-bed experiments and catalyst characterization were used to elucidate catalytic pathways that may explain the product selectivities. The effects of temperature, feed composition, and residence time were studied. The present work also investigates similarities between the Fischer-Tropsch (FT) and $CO_2$ hydrogenation processes and highlights the importance of using a high residence time for carbon chain-growth reactions similar to Fischer-Tropsch (FT).

Thermodynamic Analysis

Regardless of the products, all $CO_2$ hydrogenation processes that produce hydrocarbons are exothermic. Thus, they require a low-temperature operation to achieve high conversions. Although Eq. 1 (below) reacts $H_2$ and $CO_2$, it does not produce a hydrocarbon and thus is not considered a hydrogenation process (note that is Eq. 1 is endothermic). Considering the Le Chatelier principle, the formation of methane (Eq. 2), olefins (Eq. 3), paraffins, (Eq. 4) and methanol (Eq. 5) processes favor high pressure operation. For all species listed above, a low-temperature operation (e.g., $T \leq 200°$ C.), permits a high theoretical conversion. However, for most heterogeneous catalysts, the processes are kinetically limited at low temperatures. Metals or metal oxides are known to catalyze $CO_2$ hydrogenation in laboratory-scale fixed-bed reactors, but they have limited activity at low temperatures. Nevertheless, high conversion and $C_{2+}$ selectivity are possible at moderate temperatures (i.e., $250 \leq T \leq 350°$ C.) where metal and metal-oxide catalysts are effective.

$$CO_2 + H_2 \rightarrow CO + H_2O \quad \Delta H_{298} = 41 \ kJ \ mol^{-1}, \quad (1)$$

$$CO_2 + 4H_2 \rightarrow CH_4 + 2H_2O \quad \Delta H_{298} = -165 \ kJ \ mol^{-1}, \quad (2)$$

$$2CO_2 + 6H_2 \rightarrow C_2H_4 + 4H_2O \quad \Delta H_{298} = -127.7 \ kJ \ mol^{-1}, \quad (3)$$

$$2CO_2 + 7H_2 \rightarrow C_2H_6 + 4H_2O \quad \Delta H_{298} = -173.9 \ kJ \ mol^{-1}, \quad (4)$$

$$CO_2 + 3H_2 \leftrightarrow CH_3OH + H_2O \quad \Delta H_{298} = -49.6 \ kJ \ mol^{-1}. \quad (5)$$

Figures 1A, 1B:
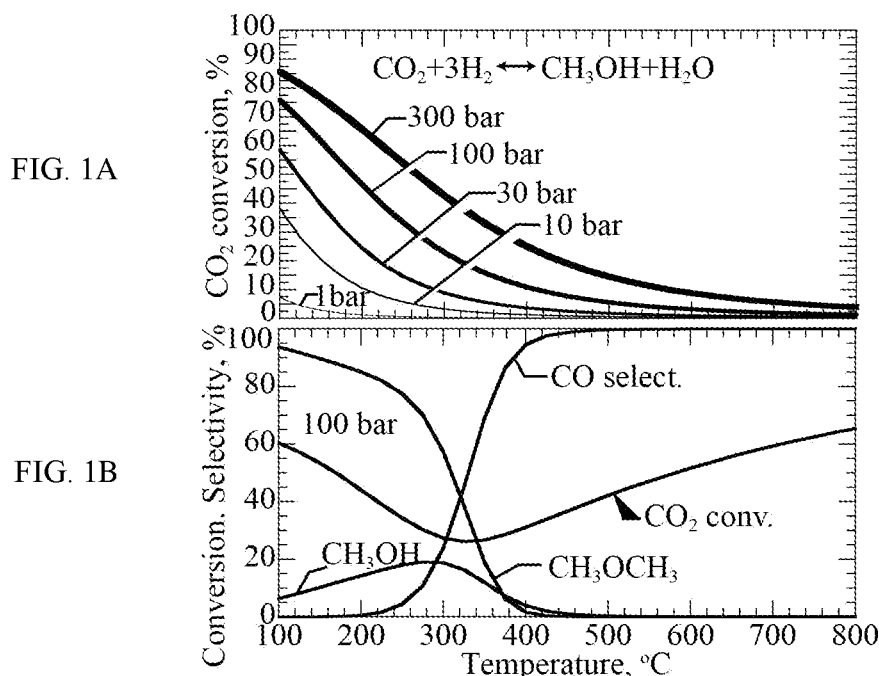
FIGS. 1A-1B.

The best-operating conditions depend on the yield and market value of the desired products as well the operational costs. Methanol and $C_2$ olefins are two high-value products that can be produced via direct $CO_2$ hydrogenation. Methanol can be used as fuel or as a commodity chemical. For example, it can also serve as an intermediate to form olefins via the methanol-to-olefin process. The challenge for methanol formation is the thermodynamic limit. The process requires working at high pressure and low temperature (FIG. 1A) to achieve reasonable conversion (e.g., ≥20%). As shown by FIG. 1B, even at relatively high pressure, the most competitive species, CO and dimethyl ether ($CH_3OCH_3$), are accompanied by methanol formation, thus significantly decreasing methanol selectivity. The process requires high pressure to sustain the high conversion. FIG. 1B shows that the temperature window for high methanol yield is relatively narrow (i.e., 250≤T≤350° C.).

The $C_{2+}$ formation route is much more viable compared to the methanol route. $CO_2$ hydrogenation permits direct formation of olefins and paraffins. Unlike methanol formation, the operating temperatures are much wider, thus permitting the use of metal or metal-oxide catalysts at moderate temperature while achieving significant conversion at relatively low pressure (e.g., 30 bar). The main drawback of the hydrocarbon-formation pathway is overcoming the thermodynamic limit of $C_{2+}$ formation. The thermodynamically more favored CO and $CH_4$ dominate over $C_{2+}$ olefins or paraffins. Despite their high yields, the value of converting $CO_2$ and $H_2$ to produce CO and $CH_4$ is questionable because of their end-use value and low energy density as a fuel. Higher value chemicals and fuels are desired to justify the costs of $H_2$ production and $CO_2$ capture. The $C_{2+}$ hydrocarbons, on the other hand, can be blended with gasoline-range fuels ($C_4$-$C_{12}$) and olefins can be used as the monomer for higher-carbon and chemicals.

Figures 2A, 2B:
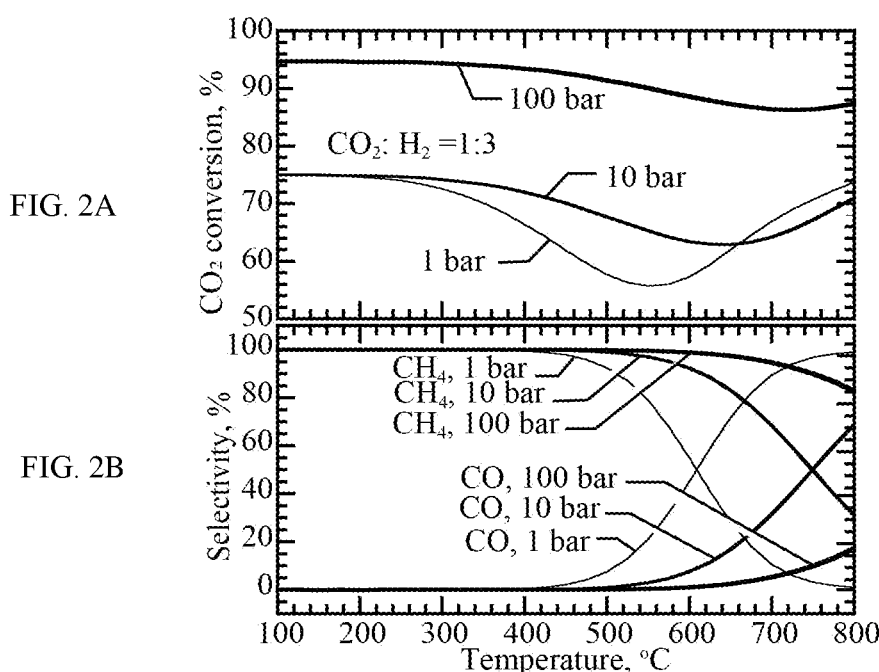
FIGS. 2A-2B.

FIGS. 2A and 2B show that the $CO_2$ hydrogenation process is extremely selective for $CH_4$ and CO formation process for a feed composition of $CO_2/H_2$=1/3 over wide temperature and pressure ranges. CO formation simply follows the Reverse Water Gas Shift (RWGS) pathway, and methane formation follows Eq. 2. In other words, increasing pressure increases $CH_4$ selectivity. FIGS. 2A and 2B show that low temperature and high-pressure favor $CH_4$ formation, while CO formation increases with increasing temperature.

Figures 3A, 3B:
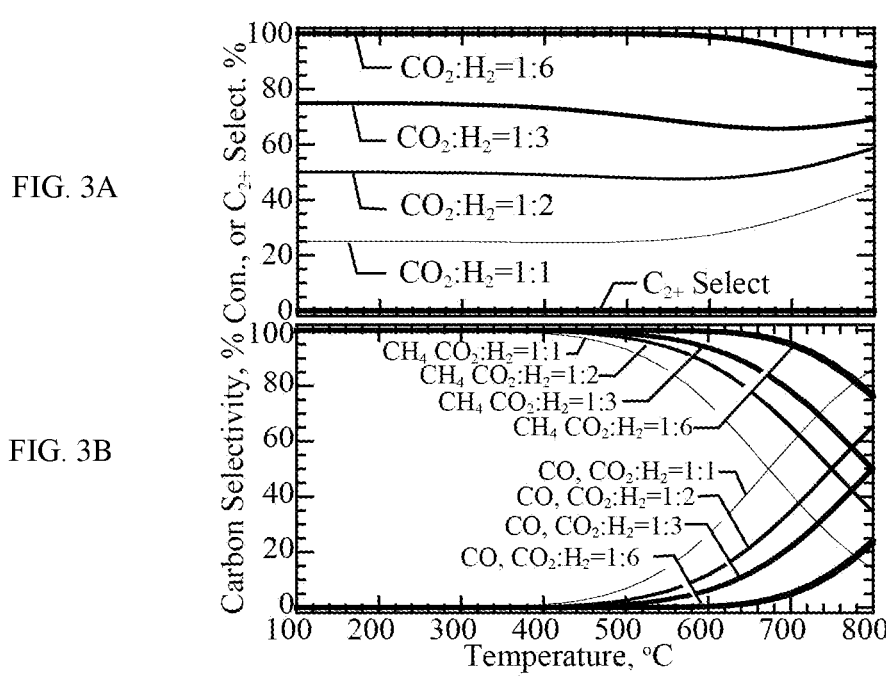
FIGS. 3A-3B.

Although FIGS. 2A and 2B do not consider carbon species other than CO and $CH_4$, FIGS. 3A and 3B show that the trends do not change even when $C_2$-$C_4$ hydrocarbons are included. FIG. 3A shows that for wide ranges of temperature and $CO_2/H_2$ ratio, the net $C_2$-$C_4$ selectivities are close to zero. Although the dominant carbon species are still CO and $CH_4$, FIG. 3B shows the equilibrium predictions of $CH_4$ and CO selectivities as functions of temperature at varying $CO_2/H_2$ ratios and 30 bar. Independent of the temperature, pressure and $CO_2/H_2$ ratios, high CO and $CH_4$ selectivity suppresses the $C_{2+}$ formation. Increasing $H_2$ partial pressure increases the $CH_4$ selectivity and $CO_2$ conversion. As the temperature increases, CO dominates over $CH_4$. To achieve a $C_{2+}$ selective process, CO and $CH_4$ formation should be suppressed by using a selective catalyst.

When $CH_4$ and CO species are not considered, FIGS. 4A and 4B show that high conversion and high $C_{2+}$ yield are theoretically possible at moderate temperature and pressure. $C_2H_6$ is thermodynamically more favorable compared to $C_2H_4$, $C_3H_6$, and $C_4H_{10}$. Increasing pressure increases the $CO_2$ conversion and favors $C_2H_6$ formation. The $C_2H_4$ formation is more favorable at temperatures above 500° C.

This thermodynamic analysis predicts that $CO_2$ hydrogenation to $C_{2+}$ is possible if ethane is more favorable compared to $C_2$ and $C_4$ alkenes. For better olefin selectivity, the catalyst should have dehydrogenation activity to promote ethane to ethylene.

Comparison of $CO_2$ hydrogenation and Fischer-Tropsch

Some similarities exist between $CO_2$ hydrogenation and Fischer-Tropsch synthesis. In both processes, high pressure and low temperature promote the production of $C_{2+}$ hydrocarbons. Higher hydrocarbon selectivity depends greatly on avoiding the undesired pathways to form $CH_4$ and CO. The $CO_2$-hydrogenation process must accommodate the additional barrier of $CO_2$ activation, making the hydrogenation process even more challenging.

When reaction conditions are suitable (i.e., 300≤T≤450° C. and elevated pressure p≥10 bar), the hydrogenation can follow a FT route to form paraffins (Eq. 6) and olefins (Eq. 7) as $$nCO + (2n+1)H_2 \rightarrow C_nH_{2n+2} + nH_2O, \qquad (6)$$

$$nCO + 2nH_2 \rightarrow C_nH_{2n} + nH_2O. \qquad (7)$$

Recognizing similar reaction pathways between the FT and $CO_2$ hydrogenation, this work refers to the $CO_2$ hydrogenation pathway as the "de-Facto FT" route. In fact, if the reverse water gas shift (RWGS) process first forms CO, the CO can undergo further hydrogenation following the FT route. Most metal-oxide catalysts (e.g., $Fe_2O_3$, $Co_2O_3$), which are active for FT, can catalyze the $CO_2$ hydrogenation process as well. The redox-active Fe-based catalysts activate the $CO_2$ via the lattice oxygen by changing its oxidation state. Because changing the Fe oxidation state is mostly controlled by temperature, the $CO_2$ activation step is often the rate-limiting step for $CO_2$ hydrogenation over redox-active metal catalysts.

Following the $CO_2$ activation, the hydrogenation process follows the FT route with olefin and paraffin products corresponding to the Anderson-Schulz-Flory (ASF) distribution, as shown in FIG. 5. For example, $C_2$-$C_4$ hydrocarbons generally cannot exceed 58 wt. %. Moreover, high $C_{2+}$ selectivity depends strongly on the $CH_4$ concentration in the product.

The traditional FT processes can operate at low temperatures (150≤T≤300° C.) or at high temperatures and at pressures typically in the range 20≤p≤40 bar. Because the de-Facto FT process requires initial $CO_2$ activation, it likely mimics the high-temperature FT process.

In a typical FT process, the chain-growth mechanism depends greatly on residence time. Practical FT processes operate with residence times in the range 30≤τ≤50 h (M. E. Dry., *J. Catal.*, 71, 227-241, 2002). If $CO_2$ hydrogenation mimics an FT pathway, $CO_2$ hydrogenation reactors should operate at similar temperatures, pressures, and residence times.

Similar to the FT process, a problem for $CO_2$ hydrogenation is catalyst stability. Relatively high temperature (i.e., 300≤T≤400° C.), a CO-rich environment, and relatively long residence times create conditions for catalyst fouling via the Bouduard reaction, $$2CO \rightarrow CO_2 + C. \qquad (8)$$

Catalyst regeneration is common in commercial FT reactors, and highly stable catalysts are needed to achieve stable long-time operation.

Fe Catalyzed $CO_2$ Hydrogenation Process

Although $FeO_xO_y$ catalysts can be effective for $CO_2$ hydrogenation, reducing the undesired bi-products CO and $CH_4$ is challenging. Furthermore, the catalysts are prone to coke formation, which makes catalyst stability a significant problem.

State of the Fe Metal

The main challenge of using an FT catalyst is that the $CO_2$ activation requires high temperatures, which is not ideal for the FT process. An $Fe_xO_y$ FT catalyst is redox active and the $CO_2$ activation follows a Mars-Van Krevelen reaction pathway. In other words, the lattice oxygen can participate in the Mars-Van Krevelen cycle to activate the $CO_2$ via Eqs. 9-10. In a $H_2$ or CO containing environment below 570° C., $Fe_2O_3$ is likely to reduce to $Fe_3O_4$ and FeO via a two-step process as $$3Fe_2O_3 + H_2 \rightarrow 2Fe_3O_4 + H_2O, \tag{9}$$

$$Fe_3O_4 + H_2 \rightarrow 3FeO + H_2O. \tag{10}$$

When an oxidizing agent such as $CO_2$ is present, the iron is re-oxidized to form $Fe^{3+}$ and $Fe^{2+}$ oxidation states via Eqs. 11 and 12, which consequently reduces the iron as $$2Fe_3O_4 + CO_2 \rightarrow 3Fe_2O_3 + CO, \tag{11}$$

$$2FeO + CO_2 \rightarrow Fe_2O_3 + CO. \tag{12}$$

Although the initial state of the Fe is as an oxide, the Fe may form an in-situ carbide structure during $CO_2$ hydrogenation. It is known that iron-carbides can be formed in-situ during the FT process due to the high affinity of CO to form iron carbides (E. de Smith et al., *Chem. Soc. Rev.*, 37, 2758-2781, 2008). The iron carbide may be in alternative crystalline forms, such as cementite ($\theta$-$Fe_3C$) and Hagg carbide ($\chi$-$Fe_5C_2$). Additionally, hexagonal iron carbides ($\varepsilon'$-$Fe_{2.2}C$, $\varepsilon$-$Fe_2C$) are also known to be present at low temperatures and/or low $H_2/CO$ ratios.

Similar to the FT process, there is evidence that $Fe_5C_2$ and $Fe_3C$ phases are formed in-situ during $CO_2$ hydrogenation (e.g., Z. Zhang et al., *J. Catal.* 390, 12-22, 2020). Catalyst pre-treatment and second-metal doping are known to affect the Fe and its stability. Zhang et al. (Y. Zhang et al., *ChemCatChem*, 10, 1272-1276, 2018) used in-operando Raman spectroscopy and X-ray diffraction, coupled with online gas chromatography, to study in-situ iron-oxide phase transformations and their effects on $CO_2$ conversion and product selectivity. They showed an in-situ transition of iron-oxide phases to iron carbide during $CO_2$ hydrogenation as $$\alpha - Fe_2O_3 \rightarrow \alpha - Fe_3O_4 \rightarrow \alpha - Fe \rightarrow \chi - Fe_5C_2, \tag{13}$$

$$\gamma - Fe_2O_3 \rightarrow \gamma - Fe_3O_4 \rightarrow \gamma - Fe \rightarrow \theta - Fe_3C. \tag{14}$$

Neither $\gamma$-$Fe_2O_3$ nor $\alpha$-$Fe_2O_3$ iron catalysts fully transform to the carbides. In other words, during in-situ carburization, iron oxide and iron carbide phases may co-exist.

In the present research, the Fe/BZY15 catalyst was subjected to carburization prior to the $CO_2$ hydrogenation process. The objective was to form the Fe-carbide, which is catalytically active for $CO_2$ hydrogenation, and thus control the phase transformation prior to hydrogenation. The characterization studies before and after the measurements indicate that the active phase for $CO_2$ hydrogenation over Fe/BZY15 catalyst is likely to be $Fe_3C$.

Experimental

Fe/BZY catalyst Preparation

The present approach used a doped-perovskite structure ($BaZr_{0.85}Y_{0.15}O_{3-\delta}$, BZY15) as the Fe support and incorporates bi-functionality that improves catalyst stability. The catalyst was prepared in a two-step process. BZY15 was first synthesized in powder form, and then $Fe_2O_3$ was introduced onto the BZY15 via the incipient wetness technique.

The BZY15 was prepared using the calcination of nitrate precursors. The metal precursors were $Ba(NO_3)_2$ (99% purity), $Zr(NO_3)_2$ (99% purity), and $Y_2O_3$ (99.9% purity). Complexing agents were ethylenediaminetetraacetic acid (EDTA, 99.4% purity), citric acid (99% purity), nitric acid (99.999% purity), and ammonium hydroxide (38-30% concentration). Powders were produced using a slightly modified EDTA-citrate complexing synthesis method. Stoichiometric amounts of nitrate metal cation precursors were combined with sufficient EDTA and citric acid to ensure complete cation mixing. The molar ratio of EDTA to citric acid to BZY powder was 2.5:1.2:1. After adding yttria ($Y_2O_3$) that was dissolved in a heated solution of water and nitric acid, the solution was heated to 80° C. as ammonium hydroxide was introduced to reduce the pH of the solution. The solution was then stirred and heated continuously until a sticky gel was formed. The gel was subsequently transferred to a drying oven at 150° C. for 12 h. The result was a BZY15 char that was subsequently calcined at 900° C. for 10 h, producing as-calcined powder with an average particle diameter of 40 nm.

The 20 wt. % Fe-containing $Fe_2O_3$/BZY15 catalyst was prepared using the incipient-wetness impregnation technique. Iron nitrate nonahydrate and BZY15 powder were premixed and diluted with water. The resulting solution was dried overnight at 80° C. while stirring. Finally, the catalyst was calcined at 500° C. for 5 h in air.

Catalyst Characterization

The fresh and used catalysts were characterized using several methods. X-ray diffraction was used to quantify the phase purity of the powders. Measurements were collected between 20 and 90°. X-ray-diffraction results were analyzed using commercial software to fit the spectra to a database of known structures. The software was able to identify multiple probable structures that account for the majority of measured peaks. Scanning transmission electron microscopy (STEM) images and energy dispersive spectroscopy (EDS) maps were also taken. The Brunauer-Emmett-Teller (BET) surface areas of the fresh Fe/BZY15 catalyst were measured using a nitrogen physisorption technique. The fresh catalyst was found to have a moderate surface area of approximately 8 $m^2$ $g^{-1}$.

Catalytic Activity Measurements

The catalytic activity of the Fe/BZY15 catalyst was measured in a laboratory-scale packed-bed reactor, as depicted in FIG. 6. The catalytic packed bed was housed within a temperature-controlled furnace. Reactive gases were controlled by digital mass-flow controllers. The reactor pressure was controlled by an automated back-pressure regulator. Premixed $CO_2$ and $H_2$ gases were fed to the reactor. Gas compositions were measured by gas chromatography (GC).

Between 0.5-1.4 grams of catalyst (250-300 µm) was mixed with approximately 1.5 g of SiC (250-300 µm) and loaded into the 0.762-cm-diameter reactor. For blank experiments, only SiC was loaded in place of the catalyst. For all experiments, thermocouples were positioned axially within the catalyst bed. The thermocouples measured the catalyst bed temperature at four points and served as control elements for the furnace temperature.

The reactor inlet and product analyses were performed online using gas chromatography with argon as an internal standard. Hydrocarbons were quantified by a calibrated flame-ionization detector while light gases and oxygenates ($H_2$, Ar, $N_2$, $CO_2$, CO) were quantified by a thermal-conductivity detector. $C_1$ to $C_{10}$ hydrocarbons, oxygenated hydrocarbons, and aromatic species were detected. The results are reported on a dry-basis. The measurements were conducted during 100 h time-on-stream experiments. No catalyst deactivation was detected.

The catalytic activity was measured for temperatures ranging as $270 \leq T \leq 375°$ C., space velocities ranging as $270 \leq T \leq 375°$ C., space velocities ranging as $0.2 \leq WHSV_{CO_2} \leq 2$ h, and feed mixtures ranging as $2 \leq CO_2/H_2 \leq 9$ at a constant pressure of 30 bar. The $WHSV_{CO_2}$ was evaluated as $$WHSV_{CO_2} = \frac{F_{CO_2} \rho_{CO_2}}{g_{cat}} \times 60. \tag{15}$$

For all experiments, the $CO_2/H_2$ ratio was adjusted by keeping the $CO_2$ flow constant and varying the $H_2$ flow rate. For the range of conditions tested, the residence times varied between $1 \leq \tau \leq 6.7$ s. The catalytic activity was reported in terms of $CO_2$ conversion and carbon selectivity. The $CO_2$ conversion was evaluated as $$X_{CO_2} = \frac{J_{CO_2 \cdot in} - J_{CO_2 \cdot out}}{J_{CO_2 \cdot in}}, \tag{16}$$

where $J_{CO_{2,in}}$ and $J_{CO_{2,out}}$ are the molar fluxes of $CO_2$ into and out of the reactor, respectively. The selectivity $S_k$ to a certain gas-phase species k was evaluated as $$S_k = C_n \frac{J_k}{J_{CO_2 \cdot in} - J_{CO_2 \cdot out}}, \tag{17}$$

where $C_n$ is the carbon number of species k (e.g., $C_2=2$ for $C_2H_6$) and $J_k$ is the outlet molar flux of species k.

Pre-Treatment

Prior to running the catalytic experiments, the catalyst was subjected to a pre-treatment regimen, i.e., carburization. To avoid a transitional behavior from iron-oxide to iron-carbide, during the reaction the catalyst was carburized and stabilized prior to the reaction. The catalyst was first reduced at ambient pressure at 500° C. for four hours in a gas environment of 20% $H_2$ and 80% Ar. Following reduction, the catalyst was carburized at ambient pressure and 500° C. for four hours in a gas environment composed of 20% $H_2$ and 80% $CH_4$. To avoid possible coke formation, the catalyst temperature was reduced to 270° C. in an environment of 20% $H_2$ and 80% Ar. Prior to introducing the reactive gases ($H_2$ and $CO_2$), the desired reactor temperature was stabilized using a feed of 95% $H_2$ and 5% Ar.

Effect of Temperature

The effect of reaction temperature was measured at 30 bar and $270 \leq T \leq 450°$ C. In all cases, 0.5 g of Fe/BZY15 was mixed with 1.5 g SiC. Table 1 lists catalyst testing conditions. After each experiment, the catalyst was regenerated by flowing 95% $H_2$ and 5% Ar before switching the operating conditions.

TABLE 1

| | Experimental conditions for evaluating the Fe/BZY15 catalyst at 30 bar | | | | |
|---|---|---|---|---|---|
| Experiment # | Temperature, ° C. | Pressure, bar | $CO_2$/ $H_2$ | Residence time (s) | $WHSV_{CO_2}$ ($h^{-1}$) |
| 1 | 270 | 30 | 1:9 | 0.8 | 2 |
| 2 | 270 | 30 | 1:6 | 1.1 | 2 |
| 3 | 270 | 30 | 1:3 | 2.0 | 2 |
| 4 | 300 | 30 | 1:9 | 0.8 | 2 |
| 5 | 325 | 30 | 1:9 | 0.8 | 2 |
| 6 | 350 | 30 | 1:9 | 0.8 | 2 |
| 7 | 350 | 30 | 1:3 | 2.0 | 2 |
| 8 | 350 | 30 | 1:6 | 1.1 | 2 |
| 9 | 375 | 30 | 1:3 | 2.0 | 2 |
| 10 | 375 | 30 | 1:6 | 1.1 | 2 |
| 11 | 375 | 30 | 1:9 | 0.8 | 2 |

Effect of Residence Time

A set of experiments was designed to measure the effect of residence time at constant pressure with varying $CO_2/H_2$ ratios. The primary purpose of these experiments was to verify that the Fe/BZY15 catalysts promote $C_{2+}$ synthesis via a high-temperature FT pathway. These experiments test the theory that increasing residence time would increase carbon chain growth following the de-Facto FT route. A constant temperature of 375° C. was chosen since the previous activity test showed significant activity at 350-375° C. A net of 1.4 g catalyst was used for the activity measurements. The catalyst was subjected to the pre-treatment regimen prior to the activity measurements.

TABLE 2

| | Experimental conditions to test the effect of residence time with varying $CO_2/H_2$ ratios at 375° C. and 30 bar | | | | |
|---|---|---|---|---|---|
| Experiment # | Temperature, ° C. | Pressure, bar | $CO_2$/ $H_2$ | Residence time (s) | $WHSV_{CO_2}$ ($h^{-1}$) |
| 1 | 375 | 30 | 1:2 | 1.7 | 0.8 |
| 2 | 375 | 30 | 1:2 | 2.7 | 0.5 |
| 3 | 375 | 30 | 1:6 | 2.9 | 0.2 |
| 4 | 375 | 30 | 1:3 | 5.0 | 0.2 |
| 5 | 375 | 30 | 1:2 | 6.7 | 0.2 |

Results and Discussion

Catalyst Characterization

FIG. 7 shows the phase analysis of the fresh Fe/BZY15 catalyst. These results indicate that the BZY sample decomposed during the infiltration process. The Fe infiltration on the BZY15 uses an acidic Fe-nitrate solution.

Decomposition of barium zirconate usually results in the formation of barium carbonate ($BaCO_3$) and zirconia ($ZrO_2$) The fresh-sample XRD pattern fits well within that trend (FIG. 7). The Fe appears to be mainly present in the system as $Fe_3O_4$, which accounts for the XRD peak at 36° (note that, while not shown here, this peak disappears in the used-sample XRD scan, FIG. 10). There is also some evidence that some Ba—Fe oxide phases are formed, which accounts for the peak at 22°. It is also important to note that there could be other phases that are not evident in the XRD spectrum.

FIG. 7 shows the elemental composition of the fresh catalyst. In FIG. 7, the barium-carbonate phase in the XRD pattern is seen clearly, with the Ba and C signals matching well. Decomposition of BZY15 phase forms nano-scale $BaCO_3$ and $ZrO_2$. There is also some evidence for $BaO_2$ and $Ba_xFe_yO_3$ phases, but this identification is less certain. Among these phases $BaCO_3$ is dominant.

As shown in the STEM/EDS mapping of FIG. 8, The Zr, Y, and Fe intensities match each other well. Yttrium likely resides as a dopant in zirconia after decomposition. Yttrium is a common dopant in zirconia, and this effect has been observed in similar decomposition processes. Higher-resolution EDS mapping, shown in FIG. 9, indicates that most of the Fe is distributed on the surface as a thin layer of nanoparticles. The XRD results shown in FIG. 7 indicate that the Fe-rich nanoparticles are likely $Fe_3O_4$. It is also possible that some Fe is in solution within the zirconia, as Fe is known to have some solid solubility in this phase.

FIG. 10 shows the XRD phase identification for a spent catalyst after 100 h of time on stream. The XRD scan of the spent sample is similar to that of the fresh sample, but with a few notable differences. The most notable difference between the two patterns (FIG. 7 and FIG. 10) is the loss of the two peaks at 36° and 38°. This indicates that the iron-oxide and the barium-iron-oxide phases from FIG. 7 are no longer present after catalytic testing. In their place, there are two likely candidates that were identified for the iron-containing phases that are present in the spent catalyst. Iron carbonate and iron carbide are both likely present in the XRD pattern, as seen in FIG. 10. The STEM/EDS mapping on spent catalysts shows clear differences in the nanostructure. Fe carbonate/carbide particles are evident in the EDS map shown in FIG. 11, and they are much larger than those in the fresh sample. Fe-rich particles have increased in size from 10-15 nm to an average of 40 nm in diameter. Higher concentrations of iron-rich particles are observed in zirconia regions in comparison to barium-carbonate regions of the catalyst.

Catalytic Experiments

FIGS. 12A and 12B show $H_2$ and $CO_2$ conversion and carbon selectivity, respectively, as a function of time-on-stream for over 100 hour. Table 1 lists the experimental conditions for each time interval. The $CO_2$ and $H_2$ conversions depend strongly on temperature. FIG. 12A shows that the process is kinetically limited below 300° C. (Experiments 1-4 in Table 1). In these intervals, the process is limited by the redox activity of the iron-oxide catalyst. Although the conversion is limited (i.e., ≤5%) at temperatures below 300° C., methanol formation is observed (i.e., ≈10% selectivity). The selectivity of methanol is low and dominated by significant CO (≈80%) and $CH_4$ (≈10%) formation.

The catalytic activity increased greatly at temperatures above 325° C., with the $CO_2/H_2$ ratio significantly influencing the $CO_2$ conversion and the product composition. Increasing the $H_2$ content increased the conversion. Under most conditions, CO and $CH_4$ dominate the product composition. When the temperature is sufficiently high, conversion reaches up to 40% at 375° C. and $CO_2/H_2=1/9$. Under these conditions, high $H_2$ content leads to high methane production, which is consistent with the thermodynamic analysis. At high temperatures, significant carbon chain growth and $C_{2+}$ formation is observed at lower $H_2$ partial pressures. These results suggest that with $CO_2/H_2<1/3$, high hydrocarbon selectivity is achieved. Decreasing $H_2$ partial pressure decreases the $CO_2$ conversion. Because the conversion increases linearly with the $H_2$ partial pressure, the hydrocarbon yield is also greatly affected by the $CO_2/H_2$ ratio.

FIG. 13 is another representation of the time-on-stream data, revealing interesting aspects of conversion and its dependence on $CO_2/H_2$ ratios at different temperatures. At temperatures above 300° C. the conversion increases linearly with increasing temperature, and the conversion is mainly controlled by the $H_2$ content. The results suggest that the chain-growth reaction is the rate-controlling step, as suggested for the FT process as well. At 270° C., the $CO_2$ conversion trend was reversed. At $CO_2/H_2=1/3$, the conversion was approximately 10%. When the $H_2$ partial pressure was increased to achieve $CO_2/H_2=1/6$, the conversion decreased to as low as 1%, and further increase of the $H_2$ partial pressure did not affect the conversion significantly. At this relatively low temperature, the catalytic activity is controlled by the redox activity of the iron-oxide. It is a kinetically limited process associated with the ability of lattice oxygen to participate in the chemistry. When the iron oxide is reduced, $CO_2$ is the dominant oxygen supplier. In these experiments, the net $CO_2$ feed rate (mol $h^{-1}$) is constant. However, when the $H_2$ partial pressure increases, it is likely to have an effect on the surface adsorbates. High $H_2$ content may block the adsorption sites for $CO_2$, thus reducing or eliminating the Fe redox cycle.

FIG. 14 is a bar graph representing the average carbon selectivities for the reaction conditions listed in Table 1. The maximum hydrocarbon selectivity is approximately 18%, with ethane and propane being the largest hydrocarbon species Small deviations from 100% carbon selectivity is due to $C_5$-$C_7$ products that are below detection. These initial catalytic activity scanning experiments help to identify temperature-dependent kinetic limitations. Results indicate that the CO can be further converted to hydrocarbons, even at high temperatures. The hydrocarbon products follow the thermodynamic trends, as illustrated in FIG. 4. $CH_4$ is the dominant hydrocarbon species. The $C_{2+}$ alkanes (i.e., $C_2H_6$ and $C_3H_8$) are favored at high temperatures above 325° C. The trend is similar to that expected from the ASF diagram (FIG. 5). The $C_2$-$C_4$ products are the dominant hydrocarbon species and their distribution is inversely correlated with $CH_4$. The decrease in $CH_4$ concentration corresponds with an increase in $C_2$-$C_4$.

Although FIGS. 12, 13, and 14 show wide ranges of temperatures and $CO_2/H_2$ ratios, the residence times for these experiments are all short (i.e., 0.8≤τ≤2 s). The results presented so far support the conjecture that $CO_2$ hydrogenation follows the trends associated with the FT process and underpinning thermodynamics More specifically the reaction conditions here are close to high-temperature Fisher-Tropsch conditions (i.e., 20-40 bar and 300-350° C.). Commercial high-temperature FT reactors operate with very long residence times on the order of 30-40 h (M. E. Dry, Ibid.).

FIG. 15 shows that chain-growth reactions for FT synthesis depend strongly on residence time. An analysis of product composition over time shows that to achieve carbon numbers of $2 \leq C_n \leq 10$, average residence times should be approximately 30 hours.

The laboratory-scale reactor used for the present study does not permit residence times greater than a few seconds. To approximate the effects of somewhat longer residence times, the catalyst loading was increased to 1.4 g. Limited by the reactor design, the residence time effect is tested between $0.8 \leq \tau \leq 6.7$ s. The relatively high temperature of 375° C. is selected because it favors high hydrocarbon formation. Low partial pressure results in a lower residence time. When $CO_2/H_2$ ratio is constant and residence time is varied by varying the total flow (Exp #1-3 in Table 2), the hydrocarbon $C_{2+}$ selectivities and conversions also increase. The $C_{2+}$ selectivity and yield are directly correlated with the residence time. The net effect of residence time on the $C_{2+}$ selectivity and yield are much more pronounced than the effects of the $CO_2/H_2$ ratio. A direct comparison of Experiments #2-3 in Table 2 with similar residence time and different $CO_2/H_2$ ratios suggests that the chain-growth reactions to produce $C_{2+}$ require long residence time. A maximum of 13% $C_{2+}$ yield and 30% hydrocarbon yield was measured at 375° C., WHSV=0.2 h$^{-1}$, and $CO_2/H_2$=1/2 at the maximum residence time of 6.7 s.

TABLE 3

Calculated conversion, hydrocarbon ($CH_4$ and $C_{2+}$) and $C_{2+}$ selectivity, and yield at different $CO_2/H_2$ ratios and residence times at 375° C. and 30 bar

| Experiment # | $CO_2/H_2$ Ratio, ° C. | Res. time (s) | WHSV$_{CO2}$ (h$^{-1}$) | HC Select., % | $C_{2+}$ Select., % | HC Yield., % | $C_{2+}$ Yield, % | Conv., % |
|---|---|---|---|---|---|---|---|---|
| 1 | 1:2 | 1.7 | 0.8 | 51.3 | 16.9 | 13.7 | 4.5 | 26.7 |
| 2 | 1:2 | 2.7 | 0.5 | 72.2 | 27.3 | 20.4 | 7.7 | 28.3 |
| 3 | 1:6 | 2.9 | 0.2 | 73.8 | 14.5 | 30.2 | 7.6 | 41.0 |
| 4 | 1:3 | 5.0 | 0.2 | 76.3 | 26.0 | 27.7 | 9.5 | 36.3 |
| 5 | 1:2 | 6.7 | 0.2 | 80.9 | 37.2 | 28.5 | 13.1 | 35.2 |

$H_2$ partial pressure favors high $C_{2+}$ selectivity. FIG. 16 shows the effect of residence time for five different experimental conditions (Table 2). The WHSV and $CO_2/H_2$ ratio are varied at 375° C. constant temperature and 30 bar pressure.

FIGS. 16A, 16B, and 16C show the results for stable time-on-stream operation for over 100 hours. FIG. 16A shows $CO_2$ and $H_2$ conversions around 40%. Although CO and $CH_4$ are the dominant products, FIGS. 16B and 16C show significant increases for higher carbon-number products. FIG. 16A shows that when $CO_2/H_2$=1/6, $CO_2$ conversion of 41% is achieved. When $CO_2/H_2$=1/2, the $CO_2$ conversion decreases to 30%. Thus, there is an evident trade-off between $CO_2$ conversion and hydrocarbon selectivity and their dependence on feed $H_2/CO_2$ ratios. FIG. 16B shows that the maximum hydrocarbon selectivity is reached when $CO_2/H_2 \leq 1/2$. Similar to the FT, ideal stoichiometry for $CO_2$ hydrogenation processes for olefin formation is $CO_2/H_2$=1/2 (Eq. 3 and Eq. 7). Although this stoichiometry is chosen for olefin formation, FIG. 16B shows that thermodynamically more favorable paraffin dominates the product. Performance could be improved by a catalyst with enhanced dehydrogenation activity.

FIG. 17 provides a summary of average carbon selectivities for the conditions listed in Table 2. The $C_{2+}$ selectivity clearly improves with increasing residence time. The $CO_2$ hydrogenation process is highly selective to paraffins over olefins, with ethane, propane, and butane being the main $C_{2+}$ hydrocarbon species. Both residence time and $CO_2/H_2$ ratio affect the conversion and hydrocarbon distribution. Long residence time improves the hydrocarbon selectivity while increasing hydrogen partial pressure shifts the selectivity toward to $CH_4$.

Table 3 reveals a clear distinction between the effects of residence time and feed $CO_2/H_2$ ratio on carbon selectivity and chain-growth. At constant WHSV$_{CO2}$, increasing the $CO_2/H_2$ ratio from 1/2 to 1/6 increases the conversion from 35% to 41%. (Experiment #3-5 in Table 2). Increased $H_2$

SUMMARY AND CONCLUSIONS

The present work demonstrates a highly stable and selective $CO_2$ hydrogenation process to form hydrocarbons over a Fe/BZY15 catalyst. The redox-active iron-oxide catalyst activates the $CO_2$ to form CO and surface oxygen. The BZY15 support contributes significantly to the catalyst stability. Although the desired hydrocarbon-product range is $C_{2+}$, the competitive methane product is also valuable.

A thermodynamic analysis was used initially to predict the theoretical limits for product distribution and identify similarities between the Fischer-Tropsch and the $CO_2$ hydrogenation processes. The effects of temperature, feed $CO_2/H_2$ ratios, and residence time were studied to understand reaction pathways and to maximize the hydrocarbon yields. The results show that a maximum 40% $CO_2$ conversion is possible with approximately 29% hydrocarbon and 13% $C_{2+}$ yields. While both the effects of temperature and feed composition impact the product composition, the controlling parameter is residence time. The $CO_2$ activation is controlled by the temperature and limited by the redox activity of the catalyst. Hydrogen partial pressure and the $CO_2/H_2$ ratio can affect the conversion and carbon selectivity. The $CO_2$ hydrogenation process may be thought of as a de-Facto FT process Similar to the FT process, the $CH_4$ and carbon number follow the Alderson-Shulz-Flory diagram (FIG. 5). To maximize the product carbon number, catalyst selectivity preferably avoids the formation of the thermodynamically most stable $CH_4$. In accordance with the thermodynamics, paraffin products dominate over olefins. The FT and $CO_2$ hydrogenation processes depend similarly on residence time. The trends suggest that the significant chain growth requires a long residence time on the order of 10 hours.

The Fe/BZY15 catalyst shows remarkable catalytic stability. No deactivation is detected for over 100 h time-on-stream measurements. The BZY15 support is believed to be responsible for catalytic stability. The XRD analysis shows that iron forms a thermodynamically stable $Fe_3C$ phase. The BZY15 perovskite phase decomposes, forming a nano-scale $BaCO_3$ phase. The results align well with prior analysis showing that the nano-scale $BaCO_3$ catalyst facilitates $CO_2$ activation. Furthermore, $BaCO_3$ is believed to improve the catalytic stability.

The results show that the highly stable Fe/BZY15 catalyst performs well for $CO_2$ hydrogenation. Although the measured $C_{2+}$ yields are moderate, higher yields are achievable with increased residence time. The process mimics the high-temperature FT pathway. Optimum yields are found for the ideal temperature ranges of $350 \leq T \leq 375°$ C. and feed ratio of $CO_2/H_2 = 1/2$. The results indicate that designing packed-bed reactors similar to the FT process can be effective. A residence time on the order of hours is preferable for achieving high $C_{2+}$ yield and $CO_2$ conversion.

While there have been shown and described what are at present considered the preferred embodiments of the invention, those skilled in the art may make various changes and modifications which remain within the scope of the invention defined by the appended claims.

What is claimed is:

1. A method of hydrogenating carbon dioxide to produce at least one hydrocarbon selected from the group consisting of methane, ethane, propane, and butane, the method comprising contacting an input gas stream containing carbon dioxide ($CO_2$) and hydrogen ($H_2$) gases with a bifunctional catalyst comprising a metal oxide in combination with a redox active ceramic support, wherein the redox active ceramic support comprises the formula $BaZr_{1-x-y-z}M^1_y M^2_z Y_x O_{3-\delta}$, wherein:

$0.1 \leq x \leq 0.2$, $0 \leq y \leq 0.8$, $0 \leq z \leq 0.8$, $0 < (x+y+z) < 1$, and $0 \leq \delta \leq 0.1$, wherein $\delta$ represents oxygen-ion vacancy;

$M^1$ and $M^2$ are selected from lanthanide elements, except that $M^2$ may alternatively be a Group 5 transition metal; and the metal oxide is selected from iron oxides and cobalt oxides and is present in the bifunctional catalyst in an amount of 10-50 wt %.

2. The method of claim 1, wherein $0 \leq y \leq 0.1$, and $0 \leq z \leq 0.1$.

3. The method of claim 1, wherein the redox active ceramic support has the formula $BaZr_{1-x}Y_x O_{3-\delta}$, wherein $0 < x \leq 0.2$.

4. The method of claim 3, wherein the redox active ceramic support has the formula $BaZr_{0.85}Y_{0.15}O_{3-\delta}$.

5. The method of claim 1, wherein $M^1$ and $M^2$ are selected from Ce and Yb.

6. The method of claim 5, wherein the redox active ceramic support has the formula $BaZr_{1-x-y-z}Ce_y Yb_z Y_x O_{3-\delta}$, wherein $0 < y \leq 0.8$, $0 < z \leq 0.2$, and $0 < (x+y+z) < 1$.

7. The method of claim 1, wherein the contacting occurs at a temperature in a range of 250° C. to 450° C.

8. The method of claim 1, wherein the contacting occurs at a temperature in a range of 300° C. to 450° C.

9. The method of claim 1, wherein the contacting occurs at a temperature in a range of 350° C. to 450° C.

10. The method of claim 1, wherein the $CO_2$ and $H_2$ gases are present in the contacting step in a $CO_2$:$H_2$ ratio of 1:10-1:1.

11. The method of claim 1, wherein the $CO_2$ and $H_2$ gases are present in the contacting step in a $CO_2$:$H_2$ ratio of 1:3-1:1.

12. The method of claim 1, wherein the $CO_2$ and $H_2$ gases are at a pressure of 10-100 atm when contacting the bifunctional catalyst.

13. The method of claim 1, wherein the $CO_2$ and $H_2$ gases are at a pressure of 20-50 atm when contacting the bifunctional catalyst.

14. The method of claim 1, wherein the $CO_2$ and $H_2$ gases make contact with the bifunctional catalyst for a gas-phase residence time of 1 second to 2 hours.

15. The method of claim 1, wherein bifunctional catalyst contains 0.1-90 wt % of the metal oxide.

16. The method of claim 1, wherein the method employs a weight hourly space velocity (WHSV) of $CO_2$ in a range of 0.2-3 $h^{-1}$.

17. The method of claim 1, wherein the method employs a weight hourly space velocity (WHSV) of $CO_2$ in a range of 0.5-2.5 $h^{-1}$.

18. The method of claim 1, wherein, prior to contacting the input gas stream with the bifunctional catalyst, the method further comprises pretreating the bifunctional catalyst by contacting the bifunctional catalyst with hydrogen gas or hydrogen-inert gas mixture at an elevated temperature of 450-600° C.

19. The method of claim 18, wherein the pretreating further comprises carburizing the bifunctional catalyst at an elevated temperature of 450-600° C. in the presence of a hydrocarbon and hydrogen gas.

20. The method of claim 1, wherein the bifunctional catalyst is contained in a packed-bed reactor.

21. The method of claim 1, wherein said at least one hydrocarbon comprises at least one selected from the group consisting of $C_2H_6$, $C_3H_8$, and $C_4H_{10}$.

22. The method of claim 1, wherein said bifunctional catalyst comprises said metal oxide incorporated into said redox active ceramic support.

* * * * *